(12) United States Patent
Reader

(10) Patent No.: US 11,154,539 B2
(45) Date of Patent: Oct. 26, 2021

(54) PHARMACEUTICAL COMPOUNDS

(71) Applicant: SAREUM LIMITED, Cambridge (GB)

(72) Inventor: John Charles Reader, Cambridge (GB)

(73) Assignee: Sareum Limited, Cambridge (GB)

( * ) Notice: Subject to any disclaimer, the term of this patent is extended or adjusted under 35 U.S.C. 154(b) by 0 days.

(21) Appl. No.: 16/343,639

(22) PCT Filed: Oct. 20, 2017

(86) PCT No.: PCT/EP2017/076909
§ 371 (c)(1),
(2) Date: Apr. 19, 2019

(87) PCT Pub. No.: WO2018/073438
PCT Pub. Date: Apr. 26, 2018

(65) Prior Publication Data
US 2019/0350905 A1    Nov. 21, 2019

(30) Foreign Application Priority Data
Oct. 21, 2016    (GB) .................... 1617871

(51) Int. Cl.
A61K 31/422    (2006.01)
A61K 31/421    (2006.01)
A61P 35/00    (2006.01)
A61K 31/454    (2006.01)
A61K 31/5377    (2006.01)
A61K 31/675    (2006.01)

(52) U.S. Cl.
CPC .......... *A61K 31/421* (2013.01); *A61K 31/422* (2013.01); *A61K 31/454* (2013.01); *A61K 31/5377* (2013.01); *A61P 35/00* (2018.01); *A61K 31/675* (2013.01)

(58) Field of Classification Search
CPC .................................................. A61K 31/422
See application file for complete search history.

(56) References Cited

U.S. PATENT DOCUMENTS

| | | | |
|---|---|---|---|
| 7,125,891 B2 | 10/2006 | Breslin et al. | |
| 8,378,095 B2 | 2/2013 | Reader et al. | |
| 8,765,734 B2 * | 7/2014 | Huang | A61K 9/0048 514/210.21 |
| 8,921,544 B2 | 12/2014 | Reader et al. | |
| 2011/0166129 A1 | 7/2011 | Machacek et al. | |
| 2013/0102592 A1 | 4/2013 | Reader et al. | |
| 2013/0143915 A1 | 6/2013 | Ellard et al. | |
| 2013/0231340 A1 * | 9/2013 | Reader | A61P 29/00 514/236.8 |

FOREIGN PATENT DOCUMENTS

| | | |
|---|---|---|
| CN | 1950347 A | 4/2007 |
| DE | 2301030 | 2/1974 |
| DE | 19653355 A1 | 6/1998 |
| DK | 200600313 L | 3/2006 |

(Continued)

OTHER PUBLICATIONS

Fontan, Cancer Discovery, 2013, vol. 3, p. 494-496 (Year: 2013).*

(Continued)

*Primary Examiner* — Karen Cheng
(74) *Attorney, Agent, or Firm* — Heslin Rothenberg Farley & Mesiti PC

(57) ABSTRACT

The invention provides a compound for use in the treatment of T-Cell Acute Lymphoblastic Leukaemia (T-ALL), the compound having the formula (1):

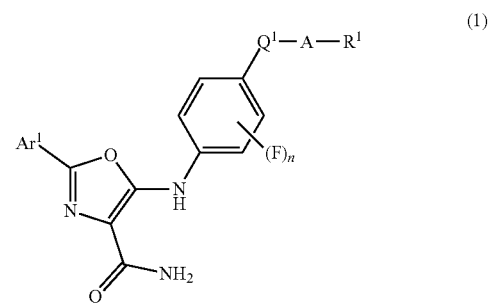

or being a pharmaceutically acceptable salt thereof; wherein:
n is 0, 1 or 2;
$Ar^1$ is selected from an optionally substituted phenyl, pyridyl, thienyl and furanyl;
$Q^1$ is selected from C(=O), S(=O) and $SO_2$;
A is absent or is $NR^2$;
$R^1$ is selected from:
  hydrogen;
  an optionally substituted $C_{1-6}$ non-aromatic hydrocarbon group; and
  optionally substituted 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings;
$R^2$ is selected from hydrogen and $C_{1-4}$ alkyl; or
$NR^1R^2$ forms an optionally substituted 4- to 7-membered non-aromatic nitrogen-containing heterocyclic ring optionally containing a second heteroatom ring member selected from nitrogen and oxygen.

8 Claims, 10 Drawing Sheets
Specification includes a Sequence Listing.

(56) References Cited

FOREIGN PATENT DOCUMENTS

| | | | |
|---|---|---|---|
| EP | 2634185 | A1 | 9/2013 |
| GB | 1374345 | | 11/1974 |
| GB | 1497536 | | 1/1978 |
| JP | 6310767 | A | 1/1988 |
| RU | 2011114992 | A | 10/2012 |
| SU | 623518 | | 9/1978 |
| WO | 0158890 | A1 | 8/2001 |
| WO | 0200649 | A1 | 1/2002 |
| WO | 2004005283 | A1 | 1/2004 |
| WO | 2005040139 | A2 | 5/2005 |
| WO | 2006095159 | A1 | 9/2006 |
| WO | 2007043400 | A1 | 4/2007 |
| WO | 2007131953 | A1 | 11/2007 |
| WO | 2008024980 | A2 | 2/2008 |
| WO | 2008139161 | A1 | 11/2008 |
| WO | WO2008139161 | * | 11/2008 |
| WO | 2008156726 | A1 | 12/2008 |
| WO | 2009155156 | A1 | 12/2009 |
| WO | 2010005841 | A1 | 1/2010 |
| WO | 2010011375 | A2 | 1/2010 |
| WO | 2010055304 | A2 | 5/2010 |
| WO | 2011113802 | A2 | 9/2011 |
| WO | 2012000970 | A1 | 1/2012 |
| WO | 2012021611 | A1 | 2/2012 |
| WO | 2013055645 | A1 | 4/2013 |
| WO | 2015032423 | A1 | 3/2015 |

OTHER PUBLICATIONS

Sanda et al., "TYK2-STAT1-BCL2-Pathway Dependence in T-cell Acute Lymphoblastic Leukemia", Cancer Discovery, vol. 3, No. 5, pp. 564-577. May 2013, published online Mar. 7, 2013.
International Search Report and Written Opinion issued in PCT/EP2017/076909 dated Jan. 5, 2018.
Argiriadi et al., "Enabling Structure-Based Drug Design of Tyk2 Through Co-Crystallization with a Stablilizing Aminoindazole Inhibitor", BMC Structural Biology, Biomed Central Ltd., London GB, vol. 12 No. 1, p. 22 (11 pages). Sep. 20, 2012.
Lykkeberg et al., "Preparation of Some 2,4-Disubstituted lmidazole-5-Carboxamides by Thermolysis of β-Substituted α-(1-Tetrazolyl) Acrylamides", Acta Chemica Scandinavica, Series B: Organic Chemistry and Biochemistry, B29(7), pp. 793-795. 1975.
Ozaki et al., "Syntheses of 5-Substituted Oxazole-4-Carboxylic Acid Derivatives with Inhibitory Activity on Blood Platelet Aggression", Chem. Pharm. Bull., 31(12), pp. 4417-4424. 1983.
Harrington et al., "VX-680, A Potent and Selective Small-Molecule Inhibitor of the Aurora Kinases, Suppresses Tumor Growth in vivo", Nature Medicine, vol. 10, No. 3, pp. 262-267. Mar. 2004.
Francheti et al., "Synthesis and Antitumor Activity of 2-β-D-Ribofuranosyloxazole-4-carboxamide", (Oxazofurin), J. Med. Chem., 33, pp. 2849-2852. 1990.
Jansen et al., Some 4-Substituted Oxazoles, J. Chem. Soc., pp. 405-411. 1961.
Morwick et al. "Evolution of the Thienopyridine Class of Inhibitors of IκB Kinase-β: Part I: Hit-to-Lead Strategies", J. Med Chem., 49, pp. 2898-2908. 2006.
Spiekermann et al., "The Protein Tyrosine Kinase Inhibitor SU5614 Inhibits FLT3 and Induces Growth Arrest and Apoptosis in AML-Derived Cell Lines Expressing a Constitutively Activated FLT3", Blood, 101(4), pp. 1494-1504. 2003.
Ponomarev et al., Zhurnal Fizicheskoi Khimii, 64(10), pp. 2723-2729 (Chem Abs. 114:100938). 1990.
Works et al., "Inhibition of TYK2 and JAK1 Amerliorates Imiquimod-Induced Psoriasis-like Dermatitis by Inhibiting L-22 and the IL-23/IL-17 Axis", The Journal of Immunology, vol. 193, 16 pages. Aug. 25, 2014.
Fleischman et al., "TNFa Facilitates Clonal Expansion of JAK2V617F Positive Cells in Myeloproliferative Neoplasms", Blood, vol. 118, No. 24, pp. 6392-6398. Dec. 8, 2011.
Leitner et al., "Tyrosine Kinase 2—Surveillant of Tumours and Bona Fide Oncogene", Cytokine, vol. 89, pp. 209-218. Available online Nov. 26, 2015.
Akahane et al., "Anti-leukaemic Activity of the TYK2 Selective Inhibitor NDI-031301 in T-cell Acute Lymphoblastic Leukaemia", British Journal of Haematology, vol. 177, pp. 271-282. Mar. 14, 2017.
Akahane et al. "Anti-Leukemic Activity of the TYK2 Selective Inhibitor ND1-031301 in T-cell Acute Lymphoblastic Leukemia" Poster. No date available.
UK Patent Office Search in GB Application No. 1617871.7, dated Aug. 8, 2017.
Thompson et al. "Photochemical Preparation of a Pyridone Containing Tetracycle: A Jak Protein Kinase Inhibitor", Bioorganic & Medicinal Chemistry Letters, vol. 12, pp. 1219-1223. 2002.

* cited by examiner

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide Substrate for TYK2 kinase
      based on mouse insulin receptor substrate 1 (IRS1)(amino acid
      979-989), where IRS1 is a membrane-proximal adaptor protein, which
      binds to, and is phosphorylated by, the insulin receptor (IR) at
      its tyrosine
<220> FEATURE:
<221> NAME/KEY: ACT_SITE
<222> LOCATION: (7)..(7)

<400> SEQUENCE: 1

Lys Lys Ser Arg Gly Asp Tyr Met Thr Met Gln Ile Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Substrate for JAK3 kinase

<400> SEQUENCE: 2

Gly Glu Glu Glu Glu Tyr Phe Glu Leu Val Lys Lys Lys Lys
1               5                   10
```

PHARMACEUTICAL COMPOUNDS

CROSS REFERENCE TO RELATED APPLICATIONS

This application is a U.S. National Phase filing under 35 U.S.C. § 371 of International Application PCT/EP2017/076909, filed Oct. 20, 2017, and published as WO 2018/073438 A1 on Apr. 26, 2018. PCT/EP2017/076909 claims priority from Great Britain application number 1617871.7, filed Oct. 21, 2016. The entire contents of each of these prior applications are hereby incorporated herein by reference.

This invention relates to compounds for use in the treatment of T-cell acute lymphoblastic leukemias, and cancers (such as hematopoietic cancers) which depend on the Janus kinase TYK2 for cancer cell survival.

BACKGROUND OF THE INVENTION

T-Cell Acute Lymphoblastic Leukaemia (T-ALL) is a rare type of leukaemia that usually occurs in late childhood or early adolescence and is significantly more common in boys than girls. T-ALL is estimated to account for 10% to 15% of pediatric acute lymphoblastic leukaemia (ALL) cases and around 200 people are diagnosed with T-ALL in the UK every year. It is aggressive and progresses quickly: about 30% of T-ALL patients relapse within the first year during or following treatment and eventually die.

As the name suggests, T-cell acute lymphoblastic leukemia affects a type of white blood cell known as T-cells. Recurrent chromosomal abnormalities are a hallmark of acute lymphoblastic leukaemias and genetic analyses of T-ALL have uncovered a substantial heterogeneity in genetic abnormalities including chromosomal translocations, deletions, amplifications, and mutations (Armstrong et al., *Journal of Clinical Oncology*, Vol. 23, No. 26, pp 6306-6315 (2005).

These genetic abnormalities result in the aberrant expression of transcription factors such as the basic helix-loop-helix (bHLH) genes MYC, TAL1 (SCL), TAL2, LYL1, or bHLHB1; genes involved in transcriptional regulation such as the cysteine-rich LIM-domain-only genes LMO1 or LMO2; or the Krüppel-like zinc-finger gene BCL11B. Abnormalities can also affect genes that are involved in embryonic development such as the homeodomain genes HOX11/TLX1 and HOX11L2/TLX3; members of the HOXA cluster; as well as signalling molecules such as the tyrosine kinase ABL13-6. Other translocations lead to the formation of specific fusion products and include CALM-AF109 or MLL rearrangements. Mutational mechanisms may also enhance gene activity as, for example, activating mutations in the NOTCH1 gene have been identified in about 50% of human T-ALLs.

Current therapy for T-ALL consists of three stages: Remission induction, consolidation, and maintenance. Remission induction is intended to rid the blood and bone marrow of leukaemia cells, requires intensive chemotherapy and involves a hospital stay of approximately 1 month. Different combinations of chemotherapy may be used, but typically involve vincristine, dexamethasone or prednisone, and doxorubicin or daunorubicin (or a similar anthracycline). Depending on the patient's prognostic factors, regimens may additionally involve cyclophosphamide, etoposide and/or high doses of methotrexate or cytarabine. These intensive treatments kill off many of the normal bone marrow cells as well as the leukaemia cells, thus serious infections or other complications can occur during this phase. CNS treatment or prophylaxis is often started during the induction phase. Most often this involves intrathecal chemotherapy (most commonly methotrexate), potentially alongside high-dose IV methotrexate or cytarabine, and radiation therapy to the brain and spinal cord.

Frequently, T-ALL goes into remission following the induction phase but, because a small number of leukaemia cells often survive the remission induction, a period of consolidation follows. Typically, this is a short course of chemotherapy using many of the drugs used during induction, and typically lasts for a few months. The drugs are usually given in high doses so that this phase of treatment is still intensive. CNS treatment may be continued during this phase. Certain patients in remission may be given the option of an allogeneic stem cell transplant (SCT), especially those with a brother or sister who would be a good donor match. An autologous SCT may be offered to those without a suitable donor. SCT is a highly risky procedure that may not benefit every patient.

After a period of consolidation, patients are generally put on a maintenance chemotherapy programme of methotrexate and 6-mercaptopurine. Occasionally this is combined with other drugs such as vincristine and prednisone. Maintenance usually lasts for about 2 years and CNS treatment may continue during this time.

Protein kinases constitute a large family of structurally related enzymes that are responsible for the control of a wide variety of signal transduction processes within the cell (Hardie and Hanks (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks and Hunter, *FASEB J.*, (1995) 9. 576-596; Knighton, et al., *Science*, (1991) 253, 407-414; Hiles, et al., *Cell*, (1992) 70, 419-429; Kunz, et al., *Cell*, (1993) 73, 585-596; Garcia-Bustos, et al., *EMBO J.*, (1994) 13, 2352-2361).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

The Janus kinase (JAK) family is a family of intracellular non-receptor tyrosine kinases, ranging in size from 120-140 kDa, that transduce cytokine-mediated signals via the JAK- STAT pathway. The JAK family plays a role in the cytokine-dependent regulation of proliferation and function of cells involved in immune response. Currently, there are four known mammalian JAK family members: JAK1, JAK2, JAK3 and TYK2. JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's.

Each JAK kinase protein has a kinase domain and a catalytically inactive pseudo-kinase domain. The JAK proteins bind to cytokine receptors through their amino-terminal FERM (Band-4.1, ezrin, radixin, moesin) domains. After the binding of cytokines to their receptors, JAKs are activated and phosphorylate the receptors, thereby creating docking sites for signalling molecules, especially for members of the signal transducer and activator of transcription (STAT) family (Yamaoka et al, 2004. The Janus kinases (Jaks). Genome Biology 5(12): 253).

In mammals, JAK1, JAK2 and TYK2 are ubiquitously expressed. The role of TYK2 in the biological response to cytokines has been characterized using a mutant human cell line that was resistant to the effects of Type I interferons (IFNs) and by demonstrating that IFNα responsiveness could be restored by genetic complementation of TYK2 (Velazquez et al, 1992. Cell 70, 313-322). Further in vitro studies have implicated TYK2 in the signalling pathways of multiple other cytokines involved in both innate and adaptive immunity. However, analysis of TYK2$^{-/-}$ mice revealed less profound immunological defects than were anticipated (Karaghiosoff et al, 2000. Immunity 13, 549-560; Shimoda et al, 2000. Immunity 13, 561-671). Surprisingly, TYK2 deficient mice display merely reduced responsiveness to IFNα/β and signal normally to interleukin 6 (IL-6) and interleukin 10 (IL-10), both of which activate TYK2 in vitro. In contrast, TYK2 was shown to be essential for IL-12 signalling with the absence of TYK2 resulting in defective STAT4 activation and the failure of T cells from these mice to differentiate into IFNy-producing ThI cells. Consistent with the involvement of TYK2 in mediating the biological effects of Type I IFNs and IL-12, TYK2$^{-/-}$ mice were more susceptible to viral and bacterial infections.

Overexpression of TYK2 kinase has been implicated in the development of some disease states. For example, elevated levels of TYK2 were found in patients suffering from progressive pulmonary sarcoidosis (Schischmanoff et al., *Sarcoidosis Vasc. Diffuse*, 2006, 23(2), 101-7).

It has been reported that JAK1 kinase is mutated in 18% of adult patients suffering from T-ALL (E. Flex et al., Journal of Experimental Medicine, 2008, 205:751-758. It has also been separately reported that T-cell acute lymphoblastic leukemias (T-ALL) account for about 15 to 25% of acute lymphoblastic leukemias in children and adults (Chiaretti et al, "T-Cell acute lymphoblastic leukemia", (2009), 94(2), 160-162). Ciarretti et al. have suggested that JAK inhibitors and in particular JAK2 inhibitors may play a role in T-ALL treatment.

Sanda et al. have reported that there is a pathway dependence on TYK2 and its downstream effector STAT1 in many (but not all) T-cell acute lymphoblastic leukemias (Sanda et al., "TYK2-STAT1-BCL2 Pathway Dependence in T-cell Acute Lymphoblastic Leukemia", (2013), Cancer Discov., 3(5), pp 564-577). Sanda et al. concluded that activation of the TYK2-STAT1 pathway in T-ALL cells occurs by gain-of-function TYK2 mutations or activation of interleukin (IL)-10 receptor signalling and that this pathway mediates T-ALL survival through upregulation of the anti-apoptotic protein BCL2. It had previously been reported (Coustan-Smith el al., "Clinical Relevance of BCL-2-Overexpression in Childhood Acute Lymphoblastic Leukemia", (1996), Blood., 87(3), pp 1140-1146) that BCL2 (B-cell lympoma 2) protein suppressed apoptosis and that elevated levels of BCL2 have been identified in acute lymphoblastic leukemia.

Sanda et al. (idem) proposed the development of molecular therapies targeting TYK2 and tested three JAK inhibitor compounds (identified only as JAK Inhibitor I, AG490 and CP-690550) having differing degrees of efficacy against TYK2 compared with other JAK family members. JAK Inhibitor I, which exhibits potent activity against all JAK family kinases, including TYK2, was found to be effective at inhibiting growth of TYK2 dependent cell lines with IC$_{50}$ values ranging from 1-3 μM, whereas a TYK2-independent cell line (LOUCY) was found to be insensitive. The compound AG490, another pan-JAK family inhibitor, produced similar results whereas the compound CP-690550, which is a potent inhibitor of JAK2 and JAK3 but not TYK2, was ineffective against the T-ALL cells.

Several JAK family inhibitors have been reported in the literature which may be useful in the medical field (Ghoreschi et al, 2009. Immunol Rev, 228:273-287). It has been proposed that a selective TYK2 inhibitor that inhibits TYK2 with greater potency than JAK2 may have advantageous therapeutic properties, because inhibition of JAK2 can cause anemia (Ghoreschi et al, 2009. Nature Immunol. 4, 356-360).

WO2012/000970 (Cellzome) discloses a series of triazolopyridines as TYK2 kinase inhibitors. WO2011/113802 (Roche) discloses a series of imidazopyridines as TYK2 kinase inhibitors. The properties of JAK kinases and their relevance as therapeutic targets are also disclosed in WO2008/156726, WO2009/155156, WO2010/005841 and WO2010/011375, all in the name of Merck.

WO2010/055304 and EP2634185 (both in the name of Sareum) disclose a family of substituted oxazole carboxamides for use in the prophylaxis or treatment of autoimmune diseases and in particular multiple sclerosis. The compounds disclosed in WO2010/055304 are described as being FLT3 kinase inhibitors. The kinase inhibiting effect of oxazole carboxamides is also disclosed in International patent application WO2008/139161 (Sareum). WO2015/032423 (Sareum) discloses the the use of a subset of oxazole carboxamides compounds as TYK2 kinase inhibitors. The compounds are described as being useful in the treatment of inflammatory and immunological disorders such as autoimmune diseases.

T-ALL is an aggressive and rapidly progressing leukaemia associated with poor patient prognoses and for which there are currently few really effective treatments. At present, therefore, remains a need for new chemotherapeutic agents for the treatment of T-ALL and, in particular, chemotherapeutic agents that not only are effective against TYK2 dependent T-ALL cells but also are effective inhibitors of at least some TYK2 independent cell lines.

THE INVENTION

It has now been found that a group of oxazole carboxamides having activity against TYK2 kinases have biological activity that suggests they will be useful in the treatment of T-ALL. Moreover, it has been found that the compounds are active not only against TYK2-dependent T-ALL cell lines but also against some TYK2-independent T-ALL cells.

Accordingly, in a first embodiment (Embodiment 1.1), the invention provides a compound for use in the treatment of T-Cell Acute Lymphoblastic Leukaemia (T-ALL), the compound having the formula (1):

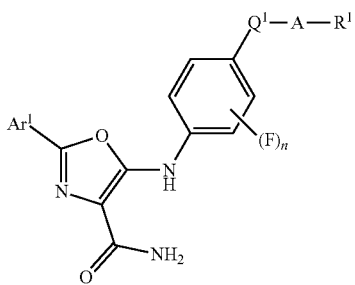

(1)

or being a pharmaceutically acceptable salt thereof; wherein:
n is 0, 1 or 2;
$Ar^1$ is selected from phenyl, pyridyl, thienyl and furanyl, each of which is optionally substituted with one, two or three substituents independently selected from halogen, $C_{1-4}$ alkyl, hydroxyl-$C_{1-4}$ alkyl, $C_{1-2}$ alkoxy-$C_{1-4}$ alkyl, $C_{1-4}$ alkoxy, $C_{1-2}$ alkoxy-$C_{1-4}$ alkoxy, $C_{2-4}$ alkenyl, $C_{2-4}$ alkenyloxy, $C_{2-4}$ alkynyl, $C_{2-4}$ alkynyloxy, cyano, $C_{1-4}$ alkanoyl, hydroxy and $C_{1-4}$ alkanoyloxy, wherein the $C_{1-4}$ alkyl and $C_{1-4}$ alkoxy moieties are each optionally substituted with one or more fluorine atoms;
$Q^1$ is selected from C(=O), S(=O) and $SO_2$;
A is absent or is $NR^2$;
$R^1$ is selected from:
  hydrogen;
  a $C_{1-6}$ non-aromatic hydrocarbon group optionally substituted with one or more substituents selected from hydroxyl, $C_{1-2}$ alkoxy, amino, mono-$C_{1-4}$ alkylamino, di-$C_{1-4}$ alkylamino, 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl or hydroxyl-$C_{1-3}$ alkyl groups; and
  3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$alkyl, mono-$C_{1-2}$ alkylamino-$C_{1-3}$ alkyl, di-$C_{1-2}$ alkylamino-$C_{1-3}$ alkyl or hydroxyl-$C_{1-3}$ alkyl groups;
$R^2$ is selected from hydrogen and $C_{1-4}$ alkyl; or
$NR^1R^2$ forms a 4- to 7-membered non-aromatic nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl amino-$C_{1-3}$alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups.

Particular compounds for use in treating T-ALL in accordance with the invention are set out below in Embodiments 1.2 to 1.88.

1.2 A compound according to Embodiment 1.1 wherein n is selected from 0 and 1.
1.3 A compound according to Embodiment 1.1 wherein n is 0.
1.4 A compound according to Embodiment 1.1 wherein n is 1.
1.5 A compound according to Embodiment 1.4 wherein the fluorine atom is attached to the benzene ring at a position ortho with respect to the moiety $Q^1$.
1.6 A compound for use according to any one of Embodiments 1.1 to 1.5 wherein $Ar^1$ is optionally substituted phenyl.
1.7 A compound for use according to any one of Embodiments 1.1 to 1.5 wherein $Ar^1$ is optionally substituted pyridyl.
1.8 A compound for use according to any one of Embodiments 1.1 to 1.5 wherein $Ar^1$ is optionally substituted thienyl.
1.9 A compound for use according to any one of Embodiments 1.1 to 1.5 wherein $Ar^1$ is optionally substituted furanyl.
1.10 A compound for use according to any one of Embodiments 1.1 to 1.9 wherein the optional substituents for $Ar^1$ are independently selected from halogen, $C_{1-4}$ alkyl, hydroxy-$C_{1-4}$ alkyl, $C_{1-2}$ alkoxy-$C_{1-4}$ alkyl, $C_{1-4}$ alkoxy, $C_{1-2}$ alkoxy-$C_{1-4}$ alkoxy, $C_{2-4}$ alkenyl, $C_{2-4}$ alkenyloxy, $C_{2-4}$ alkynyl, $C_{2-4}$ alkynyloxy, cyano, $C_{1-4}$ alkanoyl, hydroxy and $C_{1-4}$ alkanoyloxy, wherein the $C_{1-4}$ alkyl and $C_{1-4}$ alkoxy moieties are each optionally substituted with one or more fluorine atoms.
1.11 A compound for use according to Embodiment 1.10 wherein the optional substituents for $Ar^1$ are independently selected from halogen, $C_{1-3}$ alkyl, hydroxy-$C_{1-3}$ alkyl, $C_{1-2}$ alkoxy-$C_{1-3}$ alkyl, $C_{1-3}$ alkoxy, $C_{1-2}$ alkoxy-$C_{1-3}$ alkoxy, cyano, $C_{1-3}$ alkanoyl and $C_{1-3}$ alkanoyloxy, wherein the $C_{1-3}$ alkyl and $C_{1-3}$ alkoxy moieties are each optionally substituted with one or more fluorine atoms.
1.12 A compound for use according to Embodiment 1.11 wherein the optional substituents for $Ar^1$ are independently selected from fluorine, chlorine, bromine, $C_{1-3}$ alkyl, hydroxy-$C_{1-3}$ alkyl, methoxy-$C_{1-3}$ alkyl, $C_{1-3}$-alkoxy, methoxy-$C_{1-3}$ alkoxy, cyano, $C_{1-3}$ alkanoyl and $C_{1-3}$ alkanoyloxy, wherein the $C_{1-3}$ alkyl and $C_{1-3}$ alkoxy moieties are each optionally substituted with one or more fluorine atoms.
1.13 A compound for use according to Embodiment 1.12 wherein the optional substituents for $Ar^1$ are independently selected from fluorine, chlorine, bromine, methyl, ethyl, isopropyl, hydroxymethyl, hydroxyethyl, methoxyethyl, methoxy, ethoxy, isopropoxy, methoxyethoxy, cyano, acetyl, acetoxy, trifluoromethyl, trifluoromethoxy, difluoromethyl and difluoromethoxy.
1.14 A compound for use according to Embodiment 1.13 wherein the optional substituents for $Ar^1$ are independently selected from fluorine, chlorine, methyl, ethyl, isopropyl, hydroxymethyl, methoxy, ethoxy, isopropoxy, cyano, acetyl, acetoxy, trifluoromethyl, trifluoromethoxy, difluoromethyl and difluoromethoxy.
1.15 A compound for use according to Embodiment 1.14 wherein the optional substituents for $Ar^1$ are independently selected from fluorine, chlorine, methyl, ethyl, methoxy, cyano, acetyl and trifluoromethyl.
1.16 A compound for use according to Embodiment 1.15 wherein the optional substituents for $Ar^1$ are independently selected from fluorine and chlorine.
1.17 A compound for use according to Embodiment 1.16 wherein each substituent is fluorine.

1.18 A compound for use according to any one of Embodiments 1.1 to 1.17 wherein Ar¹ is unsubstituted or has 1, 2 or 3 substituents.

1.19 A compound for use according to Embodiment 1.18 wherein Ar¹ is unsubstituted.

1.20 A compound for use according to Embodiment 1.18 wherein Ar¹ has 1 substituent.

1.21 A compound for use according to Embodiment 1.18 wherein Ar¹ has 2 substituents.

1.22 A compound for use according to Embodiment 1.18 wherein Ar¹ has 3 substituents.

1.23 A compound for use according to Embodiment 1.18 wherein Ar¹ is unsubstituted or has 1 or 2 substituents.

1.24 A compound for use according to any one of Embodiments 1.1 to 1.6, 1.10 to 1.21 and 1.23 wherein Ar¹ is an unsubstituted phenyl group or a 2-monosubstituted, 3-monosubstituted, 4-monosubstituted, 2,3 disubstituted, 2,4 disubstituted, 2,5 disubstituted or 2,6 disubstituted phenyl group.

1.25 A compound for use according to Embodiment 1.24 wherein Ar¹ is selected from unsubstituted phenyl, 2-fluorophenyl, 2-hydroxyphenyl, 2-methoxyphenyl, 2-methylphenyl, 3-fluorophenyl, 3-methoxyphenyl, 2,6-difluorophenyl, 2-fluoro-3-methoxyphenyl, 2-fluoro-5-methoxyphenyl, 2-chloro-6-methoxyphenyl, 2-fluoro-6-methoxyphenyl, 2,6-dichlorophenyl, 2-chloro-6-fluorophenyl, and 5-fluoro-2-methoxyphenyl.

1.26 A compound for use according to Embodiment 1.25 wherein Ar¹ is selected from 2,6-difluorophenyl, 2-chloro-6-fluorophenyl and 2,6-dichlorophenyl.

1.27 A compound for use according to Embodiment 1.26 wherein Ar¹ is 2,6-difluorophenyl.

1.28 A compound for use according to Embodiment 1.26 wherein Ar¹ is 2-chloro-6-fluorophenyl.

1.29 A compound for use according to Embodiment 1.26 wherein Ar¹ is 2,6-dichlorophenyl.

1.30 A compound for use in the treatment of T-Cell Acute Lymphoblastic Leukaemia (T-ALL), according to Embodiment 1.1, wherein said compound is of the formula (2):

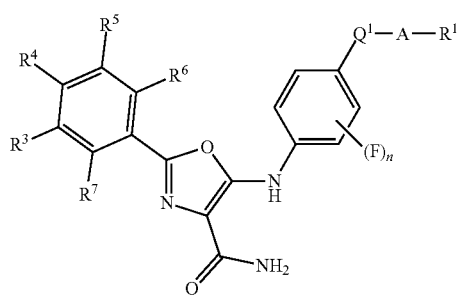

(2)

or is a pharmaceutically acceptable salt or stereoisomer thereof; wherein:

R⁷ is selected from chlorine and fluorine;
R³, R⁴, R⁵ and R⁶ are each independently selected from hydrogen, fluorine and chlorine;
n is 0, 1 or 2;
Q¹ is selected from C(=O), S(=O) and SO₂;
A is absent or is NR²;
R¹ is selected from:
  hydrogen;
  a $C_{1-6}$ non-aromatic hydrocarbon group optionally substituted with one or more substituents selected from hydroxyl, $C_{1-2}$ alkoxy, amino, mono-$C_{1-4}$ alkylamino, di-$C_{1-4}$ alkylamino, 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocylic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl or hydroxyl-$C_{1-3}$ alkyl groups; and
  3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocylic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$alkyl, mono-$C_{1-2}$ alkylamino-$C_{1-3}$ alkyl, di-$C_{1-2}$ alkylamino-$C_{1-3}$ alkyl or hydroxyl-$C_{1-3}$ alkyl groups;

R² is selected from hydrogen and $C_{1-4}$ alkyl; or
NR¹R² forms a 4- to 7-membered non-aromatic nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl amino-$C_{1-3}$alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups; with the proviso that no more than two of R³ to R⁶ are other than hydrogen.

1.31 A compound for use according to Embodiment 1.30 provided that when R⁷ and R⁶ are both fluorine, then one of R³ to R⁵ is chlorine or fluorine.

1.32 A compound for use according to Embodiment 1.30 or Embodiment 1.31 wherein R⁷ is chlorine.

1.33 A compound for use according to Embodiment 1.32 wherein R⁷ is chlorine and R⁶ is fluorine.

1.34 A compound for use according to Embodiment 1.32 wherein R⁷ and R⁶ are both chlorine.

1.35 A compound for use according to any one of Embodiments 1.30 to 1.34 wherein at least one of R³ and R⁵ is hydrogen.

1.36 A compound for use according to Embodiment 1.35 wherein both of R³ and R⁵ are hydrogen.

1.37 A compound according to any one of Embodiments 1.30 to 1.36 wherein R⁴ is hydrogen.

1.38 A compound according to any one of Embodiments 1.30 to 1.36 wherein R⁴ is fluorine.

1.39 A compound according to any one of Embodiments 1.30 to 1.36 wherein R⁴ is chlorine.

1.40 A compound for use according to any one of Embodiments 1.1 to 1.39 wherein Q¹ is C(=O).

1.41 A compound for use according to any one of Embodiments 1.1 to 1.39 wherein Q¹ is S(=O).

1.42 A compound for use according to any one of Embodiments 1.1 to 1.39 wherein Q¹ is SO₂.

1.43 A compound for use according to any one of Embodiments 1.1 to 1.42 wherein A is absent (i.e. the moieties R¹ and Q¹ are directly joined together).

1.44 A compound for use according to any one of Embodiments 1.1 to 1.39 wherein A is absent and Q¹ is SO₂.

1.45 A compound for use according to any one of Embodiments 1.1 to 1.42 wherein A is NR².

1.46 A compound for use according to any one of Embodiments 1.1 to 1.45 wherein $R^1$ is selected from:
  hydrogen;
  a $C_{1-6}$ saturated hydrocarbon group optionally substituted with one or more substituents selected from hydroxy, $C_{1-2}$ alkoxy, amino, mono-$C_{1-4}$ alkylamino, di-$C_{1-4}$ alkylamino, 3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups; and
  3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups;
$R^2$, when present, is selected from hydrogen and $C_{1-4}$ alkyl; or
$NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl or hydroxy-$C_{1-3}$ alkyl groups.

1.47 A compound for use according to Embodiment 1.46 wherein $R^1$ is selected from:
  hydrogen;
  a $C_{1-4}$ alkyl group optionally substituted with one or more substituents selected from hydroxyl, $C_{1-3}$ alkoxy, amino, mono-$C_{1-3}$ alkylamino, di-$C_{1-3}$ alkylamino, 3- to 5-membered saturated carbocyclic rings and 4- to 6-membered heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-3}$ alkoxycarbonyl, or hydroxy-$C_{1-3}$ alkyl groups; and
  3- to 5-membered saturated carbocyclic rings and 4 to 6 membered heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-4}$ alkoxycarbonyl or hydroxy-$C_{1-3}$ alkyl groups;
$R^2$, when present, is selected from hydrogen and $C_{1-2}$ alkyl; or
$NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-3}$ alkyl, $C_{1-3}$ alkanoyl, $C_{1-3}$ alkanoyloxy, $C_{1-3}$ alkoxy, $C_{1-4}$ alkoxycarbonyl or hydroxy-$C_{1-3}$ alkyl groups.

1.48 A compound for use according to Embodiment 1.46 wherein $R^1$ is selected from:
  hydrogen;
  a $C_{1-4}$ alkyl group optionally substituted with one or more substituents selected from hydroxy, amino, mono-$C_{1-3}$ alkylamino and di-$C_{1-3}$ alkylamino; and
  5 to 6-membered heterocyclic rings containing a nitrogen ring member and optionally a second ring member selected from N and O, the heterocyclic rings being optionally substituted with one or more $C_{1-3}$ alkyl or hydroxy-$C_{1-3}$ alkyl groups;
$R^2$, when present, is selected from hydrogen and $C_{1-2}$ alkyl; or
$NR^1R^2$ forms a 5 to 6-membered heterocyclic ring containing a nitrogen ring member and optionally a second ring member selected from N and O, the heterocyclic rings being optionally substituted with one or more $C_{1-3}$ alkyl or hydroxy-$C_{1-3}$ alkyl groups.

1.49 A compound for use according to Embodiment 1.46 wherein $R^1$ is selected from:
  hydrogen;
  a $C_{1-4}$ alkyl group optionally substituted with one or more substituents selected from hydroxy, amino and mono-$C_{1-3}$ alkylamino; and
  5 to 6-membered heterocyclic rings selected from pyrrolidine, piperidine, piperazine and morpholine, the heterocyclic rings being optionally substituted with one or more $C_{1-3}$ alkyl or hydroxy-$C_{1-3}$ alkyl groups;
$R^2$, when present, is selected from hydrogen and $C_{1-2}$ alkyl; or
$NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.50 A compound for use according to Embodiment 1.46 wherein $R^1$ is selected from:
  hydrogen;
  a $C_{1-3}$ alkyl group optionally substituted with one or more substituents selected from hydroxy, amino and methylamino; and
  5 to 6-membered heterocyclic rings selected from pyrrolidine, piperidine, piperazine and morpholine, the heterocyclic rings being optionally substituted with one or more $C_{1-3}$ alkyl or hydroxy-$C_{1-3}$ alkyl groups;
$R^2$, when present, is selected from hydrogen and $C_{1-2}$ alkyl; or
$NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.51 A compound for use according to Embodiment 1.46 wherein $R^1$ is selected from:
  hydrogen;
  a $C_{1-3}$ alkyl group optionally substituted with one or more substituents selected from hydroxy, amino and methylamino; and
  5 to 6-membered heterocyclic rings selected from pyrrolidine and piperidine, the heterocyclic rings being optionally substituted with a methyl group;
$R^2$, when present, is selected from hydrogen and methyl; or
$NR^1R^2$ forms a 5 to 6-membered heterocyclic ring selected from pyrrolidine and morpholine, the heterocyclic ring being optionally substituted with a hydroxymethyl group.

1.52 A compound according to any one of Embodiments 1.1 to 1.45 wherein $R^1$ is selected from:
hydrogen; and
a $C_{1-6}$ non-aromatic hydrocarbon group optionally substituted with one or more substituents selected from hydroxyl, $C_{1-2}$ alkoxy, amino, mono-$C_{1-4}$ alkylamino, di-$C_{1-4}$ alkylamino, 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl or hydroxyl-$C_{1-3}$ alkyl groups.

1.53 A compound according to any one of Embodiments Embodiments 1.1 to 1.45 wherein $R^1$ is selected from:
hydrogen; and
a $C_{1-4}$ alkyl group optionally substituted with one or more substituents selected from hydroxyl, $C_{1-3}$ alkoxy, amino, mono-$C_{1-3}$ alkylamino, alkylamino, 3- to 5-membered saturated carbocyclic rings and 4- to 6-membered heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-3}$alkoxycarbonyl, or hydroxy-$C_{1-3}$ alkyl groups.

1.54 A compound according to any one of Embodiments 1.1 to 1.45 wherein $R^1$ is selected from:
hydrogen; and
a $C_{1-4}$ alkyl group optionally substituted with one or more substituents selected from hydroxy, amino, mono-$C_{1-3}$ alkylamino and di-$C_{1-3}$ alkylamino.

1.55 A compound according to any one of Embodiments 1.1 to 1.45 wherein $R^1$ is selected from:
hydrogen;
a $C_{1-4}$ alkyl group optionally substituted with one or more substituents selected from hydroxy, amino and mono-$C_{1-3}$ alkylamino; and
5 to 6-membered non-aromatic heterocyclic rings containing a nitrogen ring member and optionally a second ring member selected from N and O, the heterocyclic rings being optionally substituted with one or more $C_{1-3}$ alkyl or hydroxy-$C_{1-3}$ alkyl groups.

1.56 A compound according to any one of Embodiments Embodiments 1.1 to 1.45 wherein $R^1$ is selected from:
hydrogen; and
a $C_{1-3}$ alkyl group optionally substituted with one or more substituents selected from hydroxy, amino and methylamino.

1.57 A compound according to Embodiment 1.56 wherein $R^1$ is a $C_{1-3}$ alkyl group.

1.58 A compound according to Embodiment 1.57 wherein $R^1$ is selected from methyl, ethyl and isopropyl.

1.59 A compound according to Embodiment 1.58 wherein $R^1$ is methyl.

1.60 A compound according to Embodiment 1.58 wherein $R^1$ is ethyl.

1.61 A compound according to Embodiment 1.58 wherein $R^1$ is isopropyl.

1.62 A compound according to Embodiment 1.56 wherein $R^1$ is a $C_{1-3}$ alkyl group optionally substituted with one or more substituents selected from hydroxy, amino and methylamino.

1.63 A compound according to Embodiment 1.62 wherein $R^1$ is a $C_{2-3}$ alkyl group substituted with one or more substituents selected from hydroxy, amino and methylamino.

1.64 A compound according to Embodiment 1.63 wherein $R^1$ is selected from 3-aminopropyl, 3-methylaminopropyl, 2-methylaminoethyl, 3-hydroxypropyl and 2-hydroxyethyl.

1.65 A compound according to Embodiment 1.56 wherein $R^1$ is hydrogen.

1.66 A compound for use according to any one of Embodiments 1.1 to 1.45 wherein $R^1$ is selected from 3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups.

1.67 A compound for use according to any one of Embodiments 1.1 to 1.45 wherein $R^1$ is selected from 3- to 5-membered saturated carbocyclic rings and 4 to 6 membered non-aromatic heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-4}$ alkoxycarbonyl or hydroxy-$C_{1-3}$ alkyl groups.

1.68 A compound for use according to any one of Embodiments 1.1 to 1.45 wherein $R^1$ is selected from 5 to 6-membered non-aromatic heterocyclic rings containing a nitrogen ring member and optionally a second ring member selected from N and O, the heterocyclic rings being optionally substituted with one or more $C_{1-3}$ alkyl or hydroxy-$C_{1-3}$ alkyl groups.

1.69 A compound for use according to any one of Embodiments 1.1 to 1.45 wherein $R^1$ is a 5- or 6-membered non-aromatic heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.70 A compound according to Embodiment 1.69 wherein $R^1$ is a 5 to 6-membered heterocyclic ring selected from pyrrolidine and piperidine, the heterocyclic ring being optionally substituted with a methyl group.

1.71 A compound for use according to any one of Embodiments 1.1 to 1.42 wherein A is $NR^2$ and $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl or hydroxy-$C_{1-3}$ alkyl groups.

1.72 A compound for use according to any one of Embodiments 1.1 to 1.42 wherein A is $NR^2$ and $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-3}$ alkyl, $C_{1-3}$ alkanoyl, $C_{1-3}$ alkanoyloxy, $C_1$-3 alkoxy, $C_{1-4}$ alkoxycarbonyl or hydroxy-$C_{1-3}$ alkyl groups.

1.73 A compound for use according to any one of Embodiments 1.1 to 1.42 wherein A is $NR^2$ and $NR^1R^2$ forms a 5 to 6-membered heterocyclic ring containing a nitrogen ring member and optionally a second ring member selected from N and O, the heterocyclic rings being optionally substituted with one or more $C_{1-3}$ alkyl or hydroxy-$C_{1-3}$ alkyl groups.

1.74 A compound for use according to any one of Embodiments 1.1 to 1.42 wherein A is $NR^2$ and $NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.75 A compound for use according to any one of Embodiments 1.1 to 1.42 wherein A is $NR^2$ and $NR^1R^2$ forms a 5 to 6-membered heterocyclic ring selected from pyrrolidine and morpholine, the heterocyclic ring being optionally substituted with a hydroxymethyl group.

1.76 A compound for use according to any one of Embodiments 1.1 to 1.42 wherein $R^2$ is selected from hydrogen and methyl.

1.77 A compound for use according to any one of Embodiments 1.1 to 1.42 and 1.45 wherein $R^2$ is hydrogen.

1.78 A compound for use according to any one of Embodiments 1.1 to 1.42 and 1.45 wherein $R^2$ is methyl.

1.79 A compound for use according to any one of Embodiments 1.1 to 1.39 wherein $Q^1$-A-$R^1$ is selected from groups AA to AT in the table below:

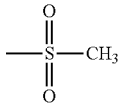 AA

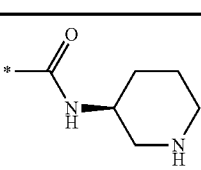 AB

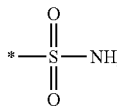 AC

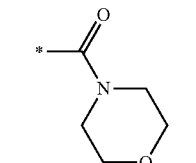 AD

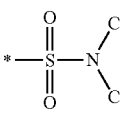 AE

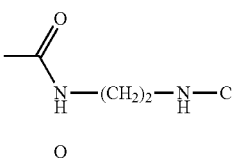 AF

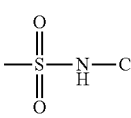 AG

-continued

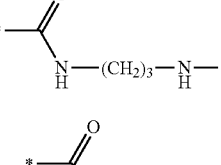 AH

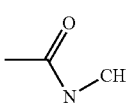 AI

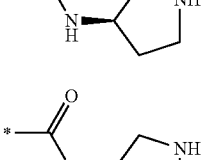 AJ

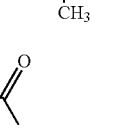 AK

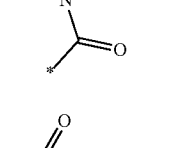 AL

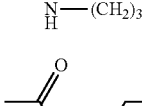 AM

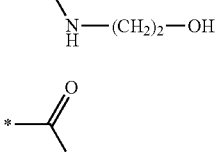 AN

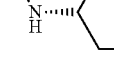 AO

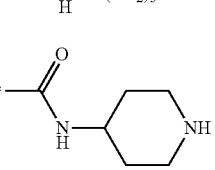 AP

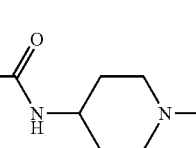 AQ

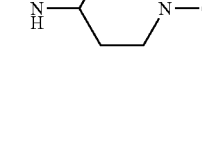 AR

-continued

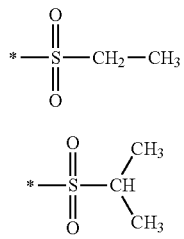

wherein the point of attachment to the phenyl group is indicated by the asterisk.

1.80 A compound according to Embodiment 1.79 wherein $Q^1$-A-$R^1$ is selected from groups AA, AG, AH, AI, AR, AS and AT.
1.81 A compound according to Embodiment 1.80 wherein $Q^1$-A-$R^1$ is selected from groups AA, AG, AH, AI and AR.
1.82 A compound for use according to Embodiment 1.81 wherein $Q^1$-A-$R^1$ is the group AA or AI.
1.83 A compound for use according to Embodiment 1.81 wherein $Q^1$-A-$R^1$ is the group AI.
1.84 A compound for use according to Embodiment 1.1 wherein the compound of formula (1) is selected from:
2-(2,6-dichloro-phenyl)-5-(4-methanesulfonyl-phenylamino)-oxazole-4-carboxylic acid amide;
2-(2-chloro-6-fluoro-phenyl)-5-(4-methanesulfonyl-phenylamino)-oxazole-4-carboxylic acid amide;
5-(4-methanesulfonyl-phenylamino)-2-(2,4,6-trifluoro-phenyl)-oxazole-4-carboxylic acid amide;
2-(2,5-difluoro-phenyl)-5-(4-methanesulfonyl-phenylamino)-oxazole-4-carboxylic acid amide;
(S) 2-(2-chloro-6-fluoro-phenyl)-5-[4-(piperidin-3-ylcarbamoyl)-phenylamino]-oxazole-4-carboxylic acid amide;
(R) 2-(2-chloro-6-fluoro-phenyl)-5-[4-(piperidin-3-ylcarbamoyl)-phenylamino]-oxazole-4-carboxylic acid amide;
2-(2-chloro-6-fluoro-phenyl)-5-[4-(morpholine-4-carbonyl)-phenylamino]-oxazole-4-carboxylic acid amide;
2-(2-chloro-6-fluoro-phenyl)-5-[4-(1-methyl-piperidin-4-ylcarbamoyl)-phenylamino]-oxazole-4-carboxylic acid amide;
(S) 2-(2,6-dichloro-phenyl)-5-[4-(piperidin-3-ylcarbamoyl)-phenylamino]-oxazole-4-carboxylic acid amide;
(R) 2-(2,6-dichloro-phenyl)-5-[4-(piperidin-3-ylcarbamoyl)-phenylamino]-oxazole-4-carboxylic acid amide;
2-(2,6-dichloro-phenyl)-5-[4-(morpholine-4-carbonyl)-phenylamino]-oxazole-4-carboxylic acid amide;
2-(2,6-dichloro-phenyl)-5-[4-(1-methyl-piperidin-4-ylcarbamoyl)-phenylamino]-oxazole-4-carboxylic acid amide;
2-(2,6-difluoro-phenyl)-5-(4-ethanesulfonyl-phenylamino)-oxazole-4-carboxylic acid amide;
2-(2,6-difluoro-phenyl)-5-(4-methanesulfonyl-phenylamino)-oxazole-4-carboxylic acid amide; and
2-(2,6-difluoro-phenyl)-5-[4-propane-2-sulfonyl)-henylamino]-oxazole-4-carboxylic acid amide;
2-(2,6-Dichloro-phenyl)-5-(4-methanesulfonyl-phenylamino)-oxazole-4-carboxylic acid amide;
2-(2-Chloro-6-fluoro-phenyl)-5-(4-methanesulfonyl-phenylamino)-oxazole-4-carboxylic acid amide;
2-(2-Chloro-6-fluoro-phenyl)-5-[4-(morpholine-4-carbonyl)-phenylamino]-oxazole-4-carboxylic acid amide; and
2-(2,6-Dichloro-phenyl)-5-[4-(morpholine-4-carbonyl)-phenylamino]-oxazole-4-carboxylic acid amide.
1.85 A compound for use according to any one of Embodiments 1.1 to 1.84 wherein the compound of formula (1) or formula (2) is in the form of a salt.
1.86 A compound for use according to Embodiment 1.85 wherein the salt is an acid addition salt.
1.87 A compound for use according to Embodiment 1.85 or Embodiment 1.86 wherein the salt is a pharmaceutically acceptable salt.
1.88 A compound for use according to any one of Embodiments 1.1 to 1.84 wherein the compound of formula (1) or formula (2) is in the form of a free base.

Definitions

The term "non-aromatic hydrocarbon group", as in "$C_{1-6}$ non-aromatic hydrocarbon group", as used herein refers to a structural group consisting of carbon and hydrogen and which does not have aromatic character.

Unless indicated otherwise, the non-aromatic hydrocarbon group can be acyclic or cyclic and can be saturated or unsaturated. Thus the term covers alkyl, alkenyl, alkynyl, cycloalkyl and cycloalkenyl groups and combinations thereof.

Where specified, non-aromatic hydrocarbon groups can be substituted; i.e. a hydrogen atom may be replaced by another atom or functional group.

References to "non-aromatic carbocyclic and heterocyclic rings" as used herein refer to both saturated and unsaturated ring systems provided that any such unsaturated ring systems do not have aromatic character, The term "bridged bicyclic heterocyclic rings" as used herein refers to non-aromatic heterocyclic ring systems in which two rings share more than two atoms, see for example Advanced Organic Chemistry, by Jerry March, 4th Edition, Wiley Interscience, pages 131-133, 1992. The bridged bicyclic ring systems can be, for example, [3.2.1] bicyclic ring systems such as an 8-aza-bicyclo[3.2.1]octane-3-yl group, or [2.2.2] bicyclic ring systems such as a quinuclidin-3-yl group.

Salts

The compounds of formula (1) or formula (2) may be presented in the form of salts.

The salts (as defined in Embodiments 1.85 to 1.87) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.86) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DLlactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Isotopes

The compounds for use according to the invention as defined in any one of Embodiments 1.1 to 1.88 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise.

For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.89), the compound for use according to any one of Embodiments 1.1 to 1.88 contains no radioactive isotopes. Such compounds are preferred for therapeutic use. In another embodiment (Embodiment 1.90), however, the compound of any one of Embodiments 1.1 to 1.88 may contain one or more radioisotopes. Compounds containing such radioisotopes may be useful in a diagnostic context.

Solvates

Compounds for use as defined in any one of Embodiments 1.1 to 1.90 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent).

Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

Accordingly, in further embodiments 1.91 and 1.92, the invention provides:
1.91 A compound for use according to any one of Embodiments 1.1 to 1.90 wherein the compound is in the form of a solvate.
1.92 A compound for use according to Embodiment 1.91 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.93), the compound for use as defined in any one of Embodiments 1.1 to 1.90 is in an anhydrous form.

Biological Activity

Compounds of the formulae (1) and (2) as defined in Embodiments 1.1 to 1.93 are inhibitors of TYK2 kinase. The TYK2 kinase-inhibiting activities of the compounds can be determined using the assays described in the Examples below. Particular compounds of formulae (1) and (2) for use in accordance with the invention are compounds having $IC_{50}$ values against TYK2 kinase in the assay described in Example 1 below of less than 50 nanomolar.

Compounds of the formulae (1) and (2) as defined in Embodiments 1.1 to 1.93 have been found to have activity against certain types of cancers in which TYK2 kinase is implicated. The cancers may be cancers in which TYK2 is required for survival; e.g. cancers in which a TYK2-STAT1-BCL2 pathway exists to prevent apoptosis of the cancer cells. Examples of such cancers include certain T-ALL cancers as described below in the experimental section of this application.

In addition to being active against TYK2-dependent T-ALL cells, it has also been found that compounds of formulae (1) and (2) as defined in Embodiments 1.1 to 1.93 have activity against certain TYK2-independent cancer cells, such as the LOUCY cell line as described below in the experimental section of this application. The basis for the activity against TYK2-independent T-ALL cell lines is currently uncertain but suggests that the compounds of formulae (1) and (2) will be useful in treating a wider range of T-ALL cancers than, for example, the JAK kinase inhibitors discussed in Sanda et al. (idem).

Accordingly, the invention also provides methods of treating cancers and uses of the compounds of formulae (1) and (2) as set out in Embodiments 2.1 to 2.13 below.
2.1 A compound of the formula (1) or (2), or a pharmaceutically acceptable salt thereof, as defined in any one of Embodiments 1.1 to 1.93 for use in the treatment of a TYK2-dependent T-Cell Acute Lymphoblastic Leukaemia.
2.2 A compound of the formula (1) or (2), or a pharmaceutically acceptable salt thereof, as defined in any one of Embodiments 1.1 to 1.93 for use in the treatment of a TYK2-independent T-Cell Acute Lymphoblastic Leukaemia.

2.3 The use of a compound of the formula (1) or (2), or a pharmaceutically acceptable salt thereof, as defined in any one of Embodiments 1.1 to 1.93 for the manufacture of a medicament for the treatment of a T-Cell Acute Lymphoblastic Leukaemia.

2.4 The use according to Embodiment 2.3 wherein the T-Cell Acute Lymphoblastic Leukaemia is selected from TYK2-dependent T-ALL and TYK2-independent T-ALL tumour types.

2.5 The use according to Embodiment 2.4 wherein the T-Cell Acute Lymphoblastic Leukaemia is selected from TYK2-dependent T-ALL tumour types.

2.6 The use according to Embodiment 2.4 wherein the T-Cell Acute Lymphoblastic Leukaemia is selected from TYK2-independent T-ALL tumour types.

2.7 A method of treating T-Cell Acute Lymphoblastic Leukaemia, which method comprises administering to a subject in need thereof a therapeutically effective amount of a compound of the formula (1) or (2), or a pharmaceutically acceptable salt thereof, as defined in any one of Embodiments 1.1 to 1.93.

2.8 A method according to Embodiment 2.7 wherein the the T-Cell Acute Lymphoblastic Leukaemia is selected from TYK2-dependent T-ALL and TYK2-independent T-ALL tumour types.

2.9 A method according to Embodiment 2.8 wherein the T-Cell Acute Lymphoblastic Leukaemia is selected from TYK2-dependent T-ALL tumour types.

2.10 A method according to Embodiment 2.8 wherein the T-Cell Acute Lymphoblastic Leukaemia is selected from TYK2-independent T-ALL tumour types.

2.11 A compound of the formula (1) or (2), or a pharmaceutically acceptable salt thereof, as defined in any one of Embodiments 1.1 to 1.93 for use in the treatment of a cancer in a patient who has been tested and diagnosed as being susceptible to treatment with a TYK2 inhibitor.

2.12 The use of a compound of the formula (1) or (2), or a pharmaceutically acceptable salt thereof, as defined in any one of Embodiments 1.1 to 1.93 for the manufacture of a medicament for the treatment of a cancer in a patient who has been tested and diagnosed as being susceptible to treatment with a TYK2 inhibitor.

2.13 A method of treating a cancer in a patient who has been tested and diagnosed as being susceptible to treatment with a TYK2 inhibitor, which method comprises administering to the patient a therapeutically effective amount of a compound of the formula (1) or (2), or a pharmaceutically acceptable salt thereof, as defined in any one of Embodiments 1.1 to 1.93.

The STAT (Signal Transducers and Activators of Transcription) family of transcription factors are downstream effectors of TYK2 kinase in the JAK/STAT cytokine signalling pathways, for example in the interleukin (IL)-10 pathway. Phosphorylation of STAT1 is seen in a number of T-ALL cell lines and many of these are TYK2 dependent (Sanda et al. "TYK2-STAT1-BCL2 Pathway Dependence in T-cell Acute Lymphoblastic Leukemia", (2013), Cancer Discov., 3(5), pp 564-577.) Aberrant activation of the TYK2-STAT1 pathway upregulates the anti-apoptotic protein, BCL2, which is required for T-ALL cells to survive.

STAT3 is frequently correlated to tumorigenesis, and is considered as an oncogene (see Pensa et al., 2009 Landes Bioscience). In particular, STAT3 constitutive activity has been reported in nearly 70% of solid and hematological tumours, including multiple myeloma, several lymphomas and leukemias, breast cancer, head and neck cancer, prostate cancer, ovarian carcinoma, melanoma, renal carcinoma, colorectal carcinoma and thymic epithelial tumours (Kortylewski et al. Targeting STAT3 affects melanoma on multiple fronts. *Cancer Metastasis Rev.* 2005; 24(2): 315-327)).

STAT5 proteins are activated by a wide variety of hematopoietic and nonhematopoietic cytokines and growth factors, all of which use the JAK-STAT signalling pathway as their main mode of signal transduction. STAT5 proteins critically regulate vital cellular functions such as proliferation, differentiation, and survival. The physiological importance of STAT5 proteins can be seen from the number of primary human tumours that have aberrant constitutive activation of these proteins, which significantly contributes to tumour cell survival and malignant progression of disease (Rani et al., *J. Interferon Cytokine Res.* 2016 April; 36(4): 226-37. doi: 10.1089/jir.2015.0054. Epub 2015 Dec. 30).

Therefore, it is envisaged that the compounds of formulae (1) and (2) and their pharmaceutically acceptable salts may be useful in treating cancers which are characterised by abnormally elevated levels of phosphorylated STAT proteins and particularly STAT1, STAT3 and STAT5 and/or abnormally elevated levels of BCL2. Accordingly, in Embodiments 2.8 to 2.13 the invention provides:

2.14 A compound of formula (1) or formula (2), or a pharmaceutically acceptable salt thereof, as defined in any one Embodiments 1.1 to 1.93 for use in the treatment or prophylaxis of a cancer characterised by abnormally elevated levels of any one or more of phosphorylated STAT1, phosphorylated STAT3 and phosphorylated STAT5.

2.15 The use of a compound of formula (1) or formula (2), or a pharmaceutically acceptable salt thereof, as defined in any one Embodiments 1.1 to 1.93 for the manufacture of a medicament for the treatment or prophylaxis of a cancer characterised by abnormally elevated levels of any one or more of phosphorylated STAT1, phosphorylated STAT3 and phosphorylated STAT5.

2.16 A method for the treatment or prophylaxis of a cancer characterised by abnormally elevated levels of any one or more of phosphorylated STAT1, phosphorylated STAT3 and phosphorylated STAT5, which method comprises administering to a patient, optionally in combination with radiotherapy, a therapeutically effective amount of a compound of formula (1) or formula (2), or a pharmaceutically acceptable salt thereof, as defined in any one Embodiments 1.1 to 1.93.

2.17 A compound of formula (1) or formula (2), or a pharmaceutically acceptable salt thereof, as defined in any one Embodiments 1.1 to 1.93 for use in the treatment or prophylaxis of a cancer characterised by abnormally elevated levels of BCL2.

2.18 The use of a compound of formula (1) or formula (2), or a pharmaceutically acceptable salt thereof, as defined in any one Embodiments 1.1 to 1.93 for the manufacture of a medicament for the treatment or prophylaxis of a cancer characterised by abnormally elevated levels of BCL2.

2.19 A method for the treatment or prophylaxis of a cancer characterised by abnormally elevated levels of BCL2, which method comprises administering to a patient a therapeutically effective amount of a compound of formula (1) or formula (2), or a pharmaceutically acceptable salt thereof, as defined in any one Embodiments 1.1 to 1.93.

2.20 A compound formula (1) or formula (2), or a pharmaceutically acceptable salt thereof, as defined in any one Embodiments 1.1 to 1.93 for use in alleviating or reducing the incidence of a cancer characterised by abnormally elevated levels of any one or more of phosphorylated STAT1, phosphorylated STAT3 and phosphorylated STAT5 and/or BCL2.

2.21 The use of a compound of formula (1) or formula (2), or a pharmaceutically acceptable salt thereof, as defined in any one Embodiments 1.1 to 1.93 for the manufacture of a medicament for alleviating or reducing the incidence of a cancer characterised by abnormally elevated levels of any one or more of phosphorylated STAT1, phosphorylated STAT3 and phosphorylated STAT5 and/or BCL2.

2.22 A method of alleviating or reducing the incidence of a cancer characterised by abnormally elevated levels of any one or more of phosphorylated STAT1, phosphorylated STAT3 and phosphorylated STAT5 and/or BCL2 in a subject (e.g. a mammalian subject, such as a human, in need thereof), which method comprises administering to the subject a therapeutically effective amount of compound of formula (1) or formula (2), or a pharmaceutically acceptable salt thereof, as defined in any one Embodiments 1.1 to 1.93.

Compounds of the invention may also be useful in treating cancers that are characterised by aberrant TYK2 kinase activation. TYK2 genomic rearrangements have been identified in studies through whole genome/transcriptome analysis of patients diagnosed with mature T-cell neoplasms or acute lymphoblastic leukaemia. A fusion of the 5' region of nucleophosmin gene (NPM1) with the 3' region of TYK2, including a part of the pseudokinase and the complete kinase domain, was revealed by RNA sequencing of a cutaneous T-cell lymphoma-derived cell line. Examination of a large cohort of mature T-cell lymphoproliferative disorders revealed TYK2 rearrangements in 15% of CD30+ lymphoproliferative disorders, including 12.5% of patients with primary anaplastic large cell lymphoma. Detailed analysis of the NPM1-TYK2 fusion protein revealed a constitutive TYK2 activation as revealed by Y1054/Y1055 phosphorylation, which in turn was shown, by phosphorylation of the appropriate tyrosine residues to lead to constitutively activated downstream effectors STAT1, STAT3 and STAT5.

Additional TYK2 fusion proteins have been reported in patients diagnosed with anaplastic large cell lymphoma. In one case the coding region of exons 1-8 of poly(A) binding protein cytoplasmic 4 (PABPC4) was fused to exons 14-23 of TYK2 (PABPC4-TYK2). In another case, a fusion of exons 1-16 of nuclear factor of kappa light polypeptide gene enhancer in B cells 2 (NFKB2) to exons 16-23 of TYK2 (NFKB2-TYK2) was observed. Ectopic expression of NFKB2-TYK2 in a HEK293 cell line led to constitutive phosphorylation of TYK2, JAK2 and STAT3, which did not occur when using a kinase-dead version of NFKB2-TYK2. It was shown that the fusion protein had oncogenic activity by transfecting NFKB2-TYK2 into mouse 3T3 fibroblasts, resulting in a larger number of colonies than in control cells.

Whether a particular cancer is of a type described above may be determined by analysing the cancer for the presence of one of the said fusion proteins.

Thus, in further embodiments (Embodiments 2.23 to 2.37, the invention provides:

2.23 A compound of formula (1) or formula (2), or a pharmaceutically acceptable salt thereof, as defined in any one of Embodiments 1.1 to 1.93 for use in treating, or alleviating or reducing the incidence of, a cancer characterised by aberrant TYK2 kinase activation.

2.24 A compound of formula (1) or formula (2), or a pharmaceutically acceptable salt thereof, as defined in any one of Embodiments 1.1 to 1.93 for use in treating, or alleviating or reducing the incidence of, a cancer characterised by aberrant TYK2 kinase activation associated with a TYK2 genomic rearrangement.

2.25 A compound of formula (1) or formula (2), or a pharmaceutically acceptable salt thereof, as defined in any one of Embodiments 1.1 to 1.93 for use in treating, or alleviating or reducing the incidence of, a cancer characterised by aberrant TYK2 kinase activation associated with fusion of a region of the TYK2 gene with another gene.

2.26 A compound for use according to Embodiment 2.25 wherein the fusion is at the 3' region of TYK2.

2.27 A compound for use according to Embodiment 2.26 wherein the fusion comprises a fusion of the 5' region of nucleophosmin gene (NPM1) with the 3' region of TYK2.

2.28 A compound for use according to Embodiment 2.25 wherein the fusion is a fusion to the exons 14-23 of TYK2.

2.29 A compound for use according to Embodiment 2.28 wherein the fusion comprises the fusion of coding region of exons 1-8 of poly(A) binding protein cytoplasmic 4 (PABPC4) to exons 14-23 of TYK2 (PABPC4-TYK2).

2.30 A compound for use according to Embodiment 2.25 wherein the fusion is a fusion to exons 16-23 of TYK2.

2.31 A compound for use according to Embodiment 2.30 wherein the fusion comprises a fusion of exons 1-16 of nuclear factor of kappa light polypeptide gene enhancer in B cells 2 (NFKB2) to exons 16-23 of TYK2 (NFKB2-TYK2).

2.32 A compound of formula (1) or formula (2), or a pharmaceutically acceptable salt thereof, as defined in any one of Embodiments 1.1 to 1.93 for use in alleviating or reducing the incidence of a cancer characterised by the presence of a fusion protein arising from the fusions of any one of Embodiments 2.25 to 2.31.

2.33 A compound for use according to Embodiment 2.32 wherein the fusion protein is a NPM1-TYK2 fusion protein.

2.34 A compound for use according to Embodiment 2.32 wherein the fusion protein is a PABPC4-TYK2 fusion protein.

2.35 A compound for use according to Embodiment 2.32 wherein the fusion protein is a NFKB2-TYK2 fusion protein.

2.36 The use of a compound of the formula (1) or (2), or a pharmaceutically acceptable salt thereof, as defined in any one of Embodiments 1.1 to 1.93 for the manufacture of a medicament for a use as defined in any one of Embodiments 2.23 to 2.35.

2.37 A method of treating a cancer in a subject (e.g. a mammalian subject such as a human), wherein the cancer is as defined in any one of Embodiments 2.23 to 2.35, which method comprises administering to the subject a therapeutically effective amount of a compound of formula (1) or (2), or a pharmaceutically acceptable salt thereof, as defined in any one of Embodiments 1.1 to 1.93.

In another general embodiment, the cancers may be such that normal TYK2 activity contributes to the hallmarks and enabling characteristics of cancer. An example of a cell extrinsic effect is the requirement of TYK2 activity in the induction of angiogenesis. Angiogenesis, the generation of new blood vessels, is essential to provide a growing tumour with nutrients and oxygen. The urokinase type plasminogen activator (uPA) and its receptor uPAR have been shown to play an important role in angiogenesis, and furthermore, that TYK2 is essential in mediating the uPA-uPAR induced signalling in vascular smooth muscle cells and glomerular mesangial cells. An example of a cell intrinsic effect, is the contribution of TYK2 to epithelial-to-mesenchymal transition (EMT), a crucial process facilitating tumour cell invasion and dissemination, During EMT/metastasis, Annexin A1 is frequently down-regulated and knockdown of Annexin A1 induces EMT in a TYK2 dependent manner. In an Eµ-Myc transgenic mouse model for human Burkitt's lymphoma, TYK2-deficient mice showed reduced invasiveness of malignant cells.

Accordingly, in further embodiments, the invention provides:

2.38 A compound of formula (1) or formula (2), or a pharmaceutically acceptable salt thereof, as defined in any one of Embodiments 1.1 to 1.93 for use in treating, or alleviating or reducing the incidence of, a cancer characterised by normal expression of TYK2 kinase (e.g. wherein the TYK2 kinase contains no detectable markers of aberrant expression).

2.39 The use of a compound of formula (1) or formula (2), or a pharmaceutically acceptable salt thereof, as defined in any one of Embodiments 1.1 to 1.93 for the manufacture of a medicament for treating, or alleviating or reducing the incidence of, a cancer characterised by normal expression of TYK2 kinase (e.g. wherein the TYK2 kinase contains no detectable markers of aberrant expression).

2.40 A method for treating, or alleviating or reducing the incidence of, a cancer in a subject (e.g. a mammalian subject such as a human), wherein the cancer is characterised by normal expression of TYK2 kinase (e.g. wherein the TYK2 kinase contains no detectable markers of aberrant expression), which method comprises administering to the subject a therapeutically effective amount of a compound of formula (1) or formula (2), or a pharmaceutically acceptable salt thereof, as defined in any one of Embodiments 1.1 to 1.93.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, bowel, colorectal, rectum and anus), liver (hepatocellular carcinoma), gall bladder and biliary system, exocrine pancreas, kidney (for example renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, testes, cervix, myometrium, endometrium, thyroid (for example thyroid follicular carcinoma), brain, adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, non-Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, neuroas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

It is envisaged that particular cancers that will be susceptible by treatment in accordance with the invention are hematopoietic cancers. Accordingly, in further embodiments, the invention provides:

2.41 The use of a compound of formula (1) or formula (2), or a pharmaceutically acceptable salt thereof, as defined in any one of Embodiments 1.1 to 1.93 for the manufacture of a medicament for the treatment or prophylaxis of a cancer (e.g. a cancer as defined herein and in particular a hematopoietic cancer) in a patient who has been tested and diagnosed as being susceptible to treatment with a TYK2 inhibitor.

2.42 A method for the prophylaxis or treatment of a cancer (e.g. a cancer as defined herein and in particular a hematopoietic cancer), which method comprises administering to a patient, who has been tested and diagnosed as being susceptible to treatment with a TYK2 inhibitor, optionally in combination with radiotherapy or another chemotherapeutic agent a compound of formula (1) or formula (2), or a pharmaceutically acceptable salt thereof, as defined in any one of Embodiments 1.1 to 1.93.

2.43 A compound of formula (1) or formula (2), or a pharmaceutically acceptable salt thereof, as defined in any one of Embodiments 1.1 to 1.93 for use in the treatment or propylaxis of a cancer (e.g. a cancer as defined herein and in particular a hematopoietic cancer) which is characterised by any one or more of aberrant expression of TYK2, and abnormally elevated levels of any one or more of phosphorylated STAT1, phosphorylated STAT3 and phosphorylated STAT5 and/or BCL2.

2.44 The use of a compound of formula (1) or formula (2), or a pharmaceutically acceptable salt thereof, as defined in any one of Embodiments 1.1 to 1.93 for the manufacture of a medicament for the treatment or prophylaxis of a cancer (e.g. a cancer as defined herein and in particular a hematopoietic cancer) which is characterised by any one or more of aberrant expression of TYK2, and abnormally elevated levels of any one or more of phosphorylated STAT1, phosphorylated STAT3 and phosphorylated STAT5 and/or BCL2.

2.45 A method for the treatment or prophylaxis of a cancer (e.g. a cancer as defined herein and in particular a hematopoietic cancer) which is characterised by any one or more of aberrant expression of TYK2, and abnormally elevated levels of any one or more of phosphorylated STAT1, phosphorylated STAT3 and phosphorylated STAT5 and/or BCL2, which method comprises administering to a patient, optionally in combination with radiotherapy or another chemotherapeutic agent a therapeutically effective amount of a compound of formula (1) or formula (2), or a pharmaceutically acceptable salt thereof, as defined in any one of Embodiments 1.1 to 1.93.

2.46 A compound of formula (1) or formula (2), or a pharmaceutically acceptable salt thereof, as defined in any one of Embodiments 1.1 to 1.93 for use in alleviating or reducing the incidence of a cancer (e.g. a cancer as defined herein and in particular a hematopoietic cancer) which is characterised by any one or more of aberrant expression of TYK2, and abnormally elevated levels of any one or more of phosphorylated STAT1, phosphorylated STAT3 and phosphorylated STAT5 and/or BCL2.

2.47 The use of a compound of formula (1) or formula (2), or a pharmaceutically acceptable salt thereof, as defined in any one of Embodiments 1.1 to 1.93 for the manufacture of a medicament for treating, or alleviating or reducing the incidence of, a cancer (e.g. a cancer as defined herein and in particular a hematopoietic cancer) which is characterised by any one or more of aberrant expression of TYK2, and abnormally elevated levels of any one or more of phosphorylated STAT1, phosphorylated STAT3 and phosphorylated STAT5 and/or BCL2.

2.48 A method of treating, or alleviating or reducing the incidence of, a cancer (e.g. a cancer as defined herein and in particular a hematopoietic cancer) which is characterised by any one or more of aberrant expression of TYK2, and abnormally elevated levels of phosphorylated STAT1, phosphorylated STAT3 and phosphorylated STAT5 and/or BCL2 in a subject (e.g. a mammalian subject, such as a human, in need thereof), which method comprises administering to the subject a therapeutically effective amount of compound of formula (1) or formula (2), or a pharmaceutically acceptable salt thereof, as defined in any one of Embodiments 1.1 to 1.93.

One particular subset of cancers against which the compounds of formulae (1) and (2) and their pharmaceutically acceptable salts should prove particularly active are cancers which are characterised by upregulation of BCL2 and/or elevated levels of phosphorylated STAT1, phosphorylated STAT3 and phosphorylated STAT5 and/or BCL2. Methods of detecting phosphorylated STAT1, STAT3 and STAT5 are well-known to those in the art and include western blotting and flow cytometry (see for example the methods used in Pratt et al., "IL-6 driven STAT signalling in circulating CD4+ lymphocytes is a marker for early anticitrullinated peptide antibody-negative rheumatoid arthritis", *Ann Rheum Dis* 2014; 0:1-8). Examples of assays for the detection of STAT1, STAT3 and STAT5 are described below in the experimental section of this application. Methods of detecting BCL2 are well-known to those in the art and include flow cytometry and western blotting (see for example the methods used in Coustan-Smith et al., "Clinical Relevance of BCL-2 Overexpression in Childhood Acute Lymphoblastic Leukemia", (1996), Blood., 87(3), pp 1140-1146.)

In particular, it has been shown that the compounds of formulae (1) and (2) and their pharmaceutically acceptable salts may be useful in the treatment of a hematopoietic cancer. The hematopoietic cancer may be a leukaemia, such as an Acute Lymphoblastic Leukaemia (for example, T-cell Acute Lymphoblastic Leukemia).

In some cancers (see for example the cell line in FIG. 2 appended hereto), STAT3 is constitutively phosphorylated. Accordingly, the invention also provides:

2.49 A compound of formula (1) or formula (2), or a pharmaceutically acceptable salt thereof, as defined in any one of Embodiments 1.1 to 1.93 for use in the treatment, or alleviating or reducing the incidence of, a cancer which is characterised by constitutive phosphorylation of STAT3.

2.50 The use of a compound of formula (1) or formula (2), or a pharmaceutically acceptable salt thereof, as defined in any one of Embodiments 1.1 to 1.93 for the manufacture of a medicament for the treatment, or alleviating or reducing the incidence of, a cancer which is characterised by constitutive phosphorylation of STAT3.

2.51 A method for the treatment, or alleviating or reducing the incidence of, a cancer in a subject (e.g. a mammalian subject such as a human), wherein the cancer is characterised by constitutive phosphorylation of STAT3, which method comprises administering to the subject an effective therapeutic amount of a compound of formula (1) or formula (2), or a pharmaceutically acceptable salt thereof, as defined in any one of Embodiments 1.1 to 1.93.

A widespread problem encountered with anti-cancer drugs is the development of drug-resistant strains of particular cancers (see Borden et al., *Frontiers in Pharmacology*, (2013) Vol. 4, Article 28, pages 1-8. Primary and acquired resistance can be caused by alterations to drug metabolism or modifications of the drug target. Resistance due to changes in drug metabolism can arise through modification of uptake, efflux and detoxification methods. Uptake could be affected by mutations that modify activity or reduce expression of surface receptors or transporters. Enhanced drug efflux can be induced by increased expression of ATP binding cassette (ABC) membrane transporters such as P-gp. Cancer cells can develop resistance to drugs requiring metabolic activation through decreased drug activation or enhanced binding of drugs by naturally occurring proteins.

Many cancer cells develop an over-reliance or dependency on an oncogene, Targetting such oncogenes forms the basis of targeted therapies. For example, gefitinib targets the epidermal growth factor receptor (EGFR) in non-small cell lung cancers. The long term effectiveness of such targeted drugs can be hindered due to the development of mutations in the kinase domain, either increasing the catalytic efficiency of the kinase, or reducing the binding interaction of the targeted therapy. Cancer cells can also circumvent the effects of targeted inhibitors by amplifying alternative oncogenes or activating alternative survival pathways.

In some drug-resistant cancers, a contributor to development of resistance is the ability of the cancer cell to bypass the biochemical pathways that are targeted by the drug. For example, acquired resistance to phosphatidylinositol 3-kinase (PI3K) inhibitors such as ZSTK474 was shown to be due to upregulation of insulin-like growth factor 1 receptor pathway, and that inhibition of this pathway with selective IGFR1 inhibitors could overcome the acquired PI3K inhibitor resistance. Resistance can also arise from evasion of apoptotic pathways triggered by the acquisition of either inactivating mutations in genes coding for apoptotic proteins such as p53 or activating mutations in genes encoding for anti-apoptotic proteins such as BCL2.

Another mechanism of cancer cell drug resistance arises from fibroblast growth factor (FGF)-2 signalling. FGF-2 can provide cancer cells with pro-survival and mitogenic signals, conferring broad-spectrum resistance to chemotherapeutic drugs. FGF-2 signalling induces the assembly of a multi-protein complex including protein kinase C (PKC)$_\varepsilon$, v-raf murine sarcoma viral oncogene homolog B1 (B-RAF) and p70 S6 kinase β (S6K2), that enhances the selective translation of anti-apoptotic proteins such as BCL-2 and inhibitors of apoptosis protein (IAP) family members which are able to protect multiple cancer cell types from chemotherapy-induced cell death. It has been shown that TYK2 is phosphorylated downstream of FGF-2 signalling and is required for the full phosphorylation of extracellular signal-regulated kinase (ERK) 1/2. Moreover TYK2 is necessary for the induction of key anti-apoptotic proteins such as BCL-2 and myeloid cell leukemia sequence (MCL) 1 to promote cell survival following FGF-2 signalling. Thus, it is envisaged that TYK2 inhibitors could enhance the effectiveness of other cancer therapies modulated by FGF-2 driven cell survival.

It is envisaged that the compounds of the present invention will be useful in treating cancers where resistance towards initial drug treatment has arisen. Thus, the compounds can be used to target a different biochemical pathway (for example TYK2-STAT1-BCL2) than the biochemical pathway targeted by the drug against which resistance has developed.

Accordingly, in a further embodiment (Embodiment 2.52), there is provided a compound of formula (1) or formula (2), or a pharmaceutically acceptable salt thereof, as defined in any one of Embodiments 1.1 to 1.93 for use in the treatment of a subject suffering from a cancer wherein the subject has been receiving drug therapy for the cancer and wherein a reduction in effectiveness indicative of drug resistance has been observed.

In another embodiment (Embodiment 2.53), there is provided a compound of formula (1) or formula (2), or a pharmaceutically acceptable salt thereof, as defined in any one of Embodiments 1.1 to 1.93 for use in the treatment of a subject suffering from a cancer wherein the subject has been receiving drug therapy for the cancer and wherein tests carried out on the subject and/or the cancer have established that the cancer is less sensitive to the drug than it was when treatment with the drug was first initiated.

In further embodiments, (Embodiments 2.54 to 2.63), the invention provides:

2.54 A method for the treatment of a subject suffering from a cancer wherein the subject has been receiving drug therapy for the cancer and wherein a reduction in effectiveness indicative of drug resistance has been observed, which method comprises administering to the subject an effective therapeutic amount of a compound of formula (1) or formula (2), or a pharmaceutically acceptable salt thereof, as defined in any one Embodiments 1.1 to 1.93.

2.55 A method for the treatment of a subject suffering from a cancer wherein the subject has been receiving drug therapy for the cancer and wherein tests carried out on the subject and/or the cancer have established that the cancer is less sensitive to the drug than it was when treatment with the drug was first initiated, which method comprises administering to the subject an effective therapeutic amount of a compound of formula (1) or formula (2), or a pharmaceutically acceptable salt thereof, as defined in any one Embodiments 1.1 to 1.93.

2.56 The use of a compound of formula (1) or formula (2), or a pharmaceutically acceptable salt thereof, as defined in any one Embodiments 1.1 to 1.93 in the manufacture of a medicament for the treatment of a cancer in a subject wherein the subject has been receiving drug therapy for the cancer and wherein tests carried out on the subject and/or the cancer have established that the cancer is less sensitive to the drug than it was when treatment with the drug was first initiated.

2.57 The use of a compound of formula (1) or formula (2), or a pharmaceutically acceptable salt thereof, as defined in any one of Embodiments 1.1 to 1.93 in the manufacture of a medicament for the treatment of a cancer in a subject wherein the subject has been receiving drug therapy for the cancer and wherein a reduction in effectiveness indicative of drug resistance has been observed.

2.58 A compound of formula (1) or formula (2), or a pharmaceutically acceptable salt thereof, as defined in any one of Embodiments 1.1 to 1.93 for use in the treatment, or alleviating or reducing the incidence of, a cancer of a type that has been shown to be resistant to one or more other chemotherapeutic agents.

2.59 The use of a compound of formula (1) or formula (2), or a pharmaceutically acceptable salt thereof, as defined in any one of Embodiments 1.1 to 1.93 for the manufacture of a medicament for the treatment, or alleviating or reducing the incidence of, a cancer of a type that has been shown to be resistant to one or more other chemotherapeutic agents.

2.60 A method for the treatment, or alleviating or reducing the incidence of, a cancer in a subject (e.g. a mammalian subject such as a human), wherein the cancer is of a type that has been shown to be resistant to one or more other chemotherapeutic agents, which method comprises administering to the subject an effective therapeutic amount of a compound of formula (1) or formula (2), or a pharmaceutically acceptable salt thereof, as defined in any one of Embodiments 1.1 to 1.93.

2.61 A compound of formula (1) or formula (2), or a pharmaceutically acceptable salt thereof, as defined in any one of Embodiments 1.1 to 1.93 for use in the treatment, or alleviating or reducing the incidence of, a cancer which is characterised by elevated levels of fibroblast growth factor (FGF)-2.

2.62 The use of a compound of formula (1) or formula (2), or a pharmaceutically acceptable salt thereof, as defined in any one of Embodiments 1.1 to 1.93 for the manufacture of a medicament for the treatment, or alleviating or reducing the incidence of, a cancer which is characterised by elevated levels of fibroblast growth factor (FGF)-2.

2.63 A method of treating, or alleviating or reducing the incidence of, a cancer in a subject (e.g. a mammalian subject such as a human), wherein the cancer is characterised by elevated levels of fibroblast growth factor (FGF)-2, which method comprises administering to the patient, a therapeutically effective amount of a compound of formula (1) or formula (2), or a pharmaceutically acceptable salt thereof, as defined in any one of Embodiments 1.1 to 1.93.

In the foregoing embodiments, the drug to which the cancer has developed resistance is typically one which does not make use of inhibition of TYK2 kinase as its primary anti-cancer effect. More particularly, the drug is one which has an $IC_{50}$ of greater than 20 μM against TYK2 kinase in a kinase inhibition assay, and more usually greater than 50 μM (for example in the range 50-500 μM. In one embodiment, the drug to which the cancer has developed resistance is substantially inactive against TYK2 kinase.

The compounds of the invention can also be used for the treatment of a cancer in a patient who has not previously received chemotherapy for the treatment of that cancer, and wherein the cancer is known to be resistant to one or more anti-cancer drugs.

In each of the foregoing embodiments 2.52 to 2.63, the drug-resistant cancer can be selected from categories A to H below and any one or more individual combinations of drugs and cancers disclosed therein:

A. Cells that have shown intrinsic or acquired resistance to DNA-binding agents such as:
Cis-platin, Oxaliplatin, Carboplatin, Cyclophosphamide, Melphalan, Temazolomide,
Carmustine, Ifosfamide, Streptozotocin, Epirubicin, Doxorubicin, Dactinomycin;
in cancers such as:
brain, testicular, head and neck cancers, Hodgkin's disease, pancreatic, ovarian, bladder, breast and lung cancers, acute leukaemias, endometrial, thyroid, Wilm's tumour, Ewing's sarcoma, rhabdomyelosarcoma and neuroblastoma (NB resistance to cis-platin has been shown to be overcome in non-small cell lung cancer using the JAK/STAT inhibitor ruxolitinib);

B. Cells that have shown intrinsic or acquired resistance to Topoisomerase I and II inhibitors such as:
Etoposide, Topotecan, Irinotecan;
in cancers such as:
Lung cancer, Kaposi's sarcoma, breast, ovarian, colon and rectal cancer;

C. Cells that have shown intrinsic or acquired resistance to Anti-metabolites such as:
Methotrexate, 5-Fluorouracil, Cytarabine, Gemcitabine, Capecitabine, 6-Mercaptopurine, 6-Thioguanine;
in cancers such as:
Acute lymphoblastic leukaemia, choriocarcinoma, breast, head and neck, lung, cervical, basal cell skin, gastrointestinal, colon, stomach, rectum, pancreas, prostate and bladder cancers, acute and chronic myelogenous leukaemia, acute lymphocytic leukaemia and acute myelomonocytic leukaemia;

D. Cells that have shown intrinsic or acquired resistance to mitotic spindle inhibitors such as:
Vincristine, Vinblastine, Paclitaxel, Docetaxel
in cancers such as:
acute lymphocytic leukaemia, Wilm's tumour, rhabdomeyelosarcoma, breast, cervical, ovarian and testicular cancers, Hodgkin's disease, Kaposi's sarcoma, and lung, bladder, head and neck cancers.

E. Cells that have shown intrinsic or acquired resistance to kinase inhibitors such as:
Dasatinib, Erlotinib, Gefitinib, Imatinib, Lapatinib, Nilotinib, Sorafenib, Sunitinib, Afatinib, Axitinib, Bosutinib, Crizotinib, Cobimetinib, Cabozantinib, Ibrutinib, Pazopanib, Ruxolitinib, Vemurafenib, Temsirolimus, Everolimus
in cancers such as:
lung and renal cancers, chronic myelogenous leukaemia, melanoma, thyroid cancer, neuroblastoma, gastrointestinal stromal tumours, breast cancer, myelofibrosis, lymphoma, and neuroendocrine tumours of the pancreas.

F. Cells that have shown intrinsic or acquired resistance to Aromatase inhibitors such as:
Anastrozole, Letrozole, Exemestane
in cancers such as:
breast cancer.

G. Cells that have shown intrinsic or acquired resistance to proteasome inhibitors such as:
Bortezomib
in cancers such as multiple myeloma; and H. Cells that have shown intrinsic or acquired resistance to other small-molecule or monoclonal antibody cancer therapies such as:
Vorinostat, Abiraterone, Venetoclax, Trastuzumab, Bevacizumab, Rituximab, Ipilimumab, Pembrolizumab, nivolumab.
in cancers such as:
T-cell lymphoma, prostate cancer, chronic lymphocytic leukaemia, melanoma and Hodgkin's lymphoma.

Methods for the Preparation of Compounds of Formula (1)

The compounds of formulae (1) and (2) and their pharmaceutically acceptable salts can be prepared by the methods described in International patent application WO2008/139161 (Sareum) and International patent application WO 2015/032423 (Sareum).

Pharmaceutical Formulations

While it is possible for the active compound to be administered alone, it is preferable to present it as a pharmaceutical composition (e.g. formulation) comprising at least one active compound of the invention together with one or more pharmaceutically acceptable excipients such as carriers, adjuvants, diluents, fillers, buffers, stabilisers, preservatives, lubricants, or other materials well known to those skilled in the art, and optionally other therapeutic or prophylactic agents.

The term "pharmaceutically acceptable" as used herein refers to compounds, materials, compositions, and/or dosage forms which are, within the scope of sound medical judgment, suitable for use in contact with the tissues of a subject (e.g. human) without excessive toxicity, irritation, allergic response, or other problems or complication, commensurate with a reasonable benefit/risk ratio. Each excipient must also be "acceptable" in the sense of being compatible with the other ingredients of the formulation.

The pharmaceutical compositions can be in any form suitable for oral, parenteral, topical, intranasal, ophthalmic, optic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formulae (1) and (2), or their pharmaceutically acceptable salts, can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively releasing the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Compositions for parenteral administration may be formulated for administration as discrete dosage units or may be formulated for administration by infusion.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Methods of Treatment

It is envisaged that the compounds of the formulae (1) and (2) and their pharmaceutically acceptable salts as defined in any one of Embodiments 1.1 to 1.93 will be useful in the prophylaxis or treatment of proliferative diseases, such as cancer, and in particular in the prophylaxis or treatment of hematopoietic cancers, particularly T-ALL. Examples of such cancers are set out above.

The compounds will typically be administered in amounts that are therapeutically or prophylactically useful and which generally are non-toxic. However, in certain situations (for example in the case of life threatening diseases), the benefits of administering a compound of the formulae (1) or (2), or a pharmaceutically acceptable salt thereof, may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively, they may be administered in a pulsatile or continuous manner.

The compound of formula (1) or (2), or a pharmaceutically acceptable salt thereof, will generally be administered to a subject in need of such administration, for example a human patient.

A typical daily dose of the compound can be up to 1000 mg per day, for example in the range from 0.01 milligrams to 10 milligrams per kilogram of body weight, more usually from 0.025 milligrams to 5 milligrams per kilogram of body weight, for example up to 3 milligrams per kilogram of bodyweight, and more typically 0.15 milligrams to 5 milligrams per kilogram of bodyweight although higher or lower doses may be administered where required.

By way of example, an initial starting dose of 12.5 mg may be administered 2 to 3 times a day. The dosage can be increased by 12.5 mg a day every 3 to 5 days until the maximal tolerated and effective dose is reached for the individual as determined by the physician. Ultimately, the quantity of compound administered will be commensurate with the nature of the disease or physiological condition being treated and the therapeutic benefits and the presence or absence of side effects produced by a given dosage regimen, and will be at the discretion of the physician.

The compounds of the formulae (1) and (2) or their pharmaceutically acceptable salts can be administered as the sole therapeutic agent or they can be administered in combination therapy with one or more other compounds such as steroids or interferons.

Combination Therapy

It is envisaged that the compounds of Embodiments 1.1 to 1.93 will be useful either as sole chemotherapeutic agents or, more usually, in combination therapy with chemotherapeutic agents or radiation therapy in the prophylaxis or treatment of a range of proliferative disease states or conditions. Examples of such disease states and conditions are set out above.

Particular examples of chemotherapeutic agents that may be co-administered with the compounds of Embodiments 1.1 to 1.93 include:

Topoisomerase I inhibitors
Antimetabolites: (e.g. Cytarabine)
Tubulin targeting agents
DNA binder and topoisomerase II inhibitors
EGFR inhibitors (e.g. Gefitinib—see Biochemical Pharmacology 78 2009 460-468)
mTOR inhibitors (e.g. Everolimus)
PI3K pathway inhibitors (e.g. PI3K, PDK1)
Akt inhibitors
Alkylating Agents (e.g. temozolomide)
Monoclonal Antibodies.
Anti-Hormones
Signal Transduction inhibitors
Proteasome Inhibitors
DNA methyl transferase inhibitors
Cytokines and retinoids
Hypoxia triggered DNA damaging agents (e.g. Tirapazamine)
Aromatase inhibitors
Anti Her2 antibodies, (see for example http://www.wipo.int/pctdb/en/wo.jsp?wo=2007056118)
Anti cd20 antibodies
Inhibitors of angiogenesis
HDAC inhibitors
MEK inhibitors
B-Raf inhibitors
ERK inhibitors
HER2 small molecule inhibitors e.g. lapatinib
Bcr-Abl tyrosine-kinase inhibitors e.g. imatinib
CDK4/6 inhibitor e.g. Ibrance
Mps1/TTK inhibitors
Aurora B inhibitors
FLT3 kinase inhibitors
IDH1 or IDH2 inhibitors
BRD4 inhibitors
Inhibitors of immune checkpoint blockade signalling components including PD1, PDL-1 and CTLA4; and steroidal compounds.

In one embodiment, the compounds of Embodiments 1.1 to 1.93 may be administered in combination with an alkylating agent. Examples of alkylating agents include nitrogen mustards (e.g. cyclophosphamide, chlormethine and uramustine), nitrosoureas, alkyl sulfonates and platinum-based chemotherapeutics. In a particular embodiment, the alkylating agent is cyclophosphamide.

Methods of Diagnosis

Prior to administration of a compound of the formula (1) or (2), or a pharmaceutically acceptable salt thereof, a patient may be screened to determine whether a disease or condition, and in particular a cancer, from which the patient is or may be suffering is one which would be susceptible to treatment with a compound having activity against TYK2.

A subject (e.g. patient) may be subjected to a diagnostic test to detect a marker indicative of the presence of a cancer in which TYK2 is implicated, or a marker indicative of susceptibility to the said cancer. For example, subjects may be screened for genetic markers indicative of the activation of the TYK2-STAT1 pathway, such as BCL2. This activation may occur as a result of a genetic mutation in the TYK2 gene or activation of interleukin (IL)-10 signalling.

The genetic marker can comprise a particular allele or single nucleotide polymorphism of the TYK2 gene which is indicative of susceptibility to cancers, such as T-ALL cancers (see for example Sanda et al., Cancer Discov., (2013), 3(5), pp 564-577.) The genetic marker can, for example, be a single nucleotide polymorphism in the TYK2 gene, or it can be a haplotype comprising a single nucleotide polymorphism in the TYK2 gene and a polymorphism in another gene.

The diagnostic tests are typically conducted on a biological sample selected from blood samples, biopsy samples, stool biopsies, sputum, chromosome analysis, pleural fluid, peritoneal fluid, or urine.

Methods of identifying genetic markers such as single nucleotide polymorphisms are well known. Examples of suitable methods for identifying such markers are described in Tomasson et al., "Somatic mutations and germline sequence variants in the expressed tyrosine kinase genes of patients with de novo acute myeloid leukemia", Blood, 1 May 2008, 111, 9, 4797.

EXAMPLES

Figure 1A:
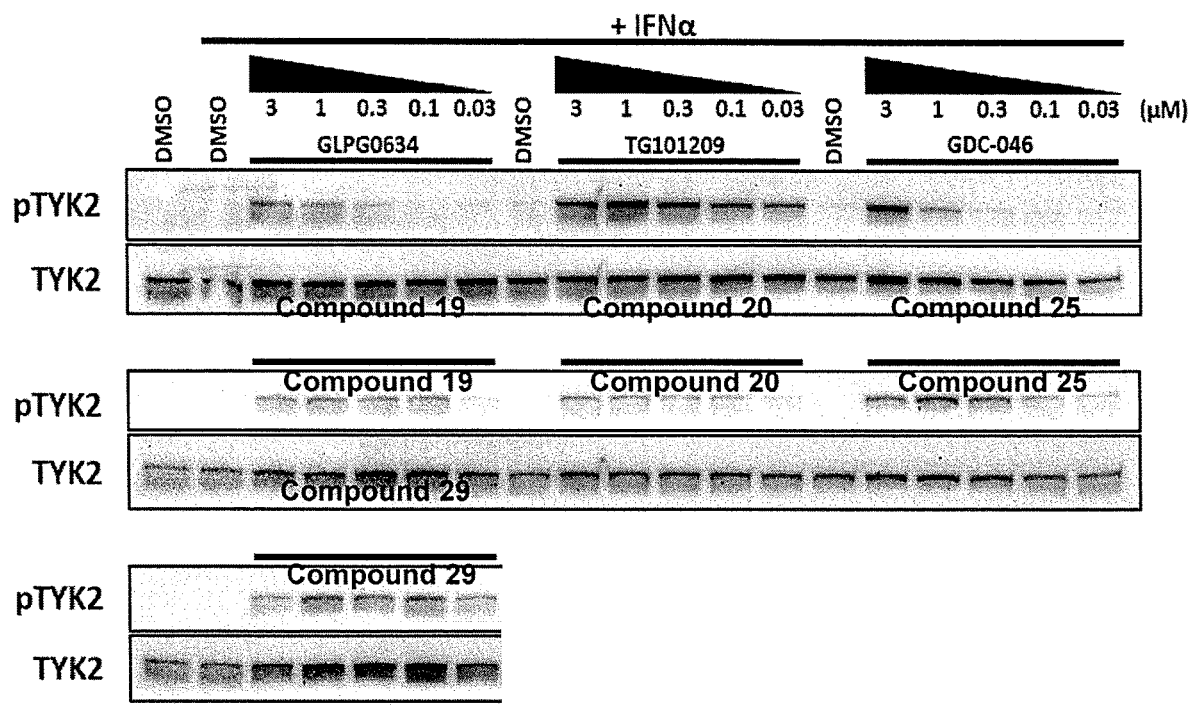
FIGS. 1A to 1E show Western Blot analyses of cell lysates obtained by incubating Jurkat cells with Compounds 19, 20, 25 and 29 and three benchmark inhibitors (GLPG0634 (Filgotinib, developed by Galapagos), TG101209 and GDC-046) as comparative examples and then probing with antibodies against phospho-TYK2/total-TYK2, phospho-STAT1/total-STAT1, phospho-STAT3/total-STAT3, phospho-STAT5/total-STAT5 and Actin.
Figure 1B:
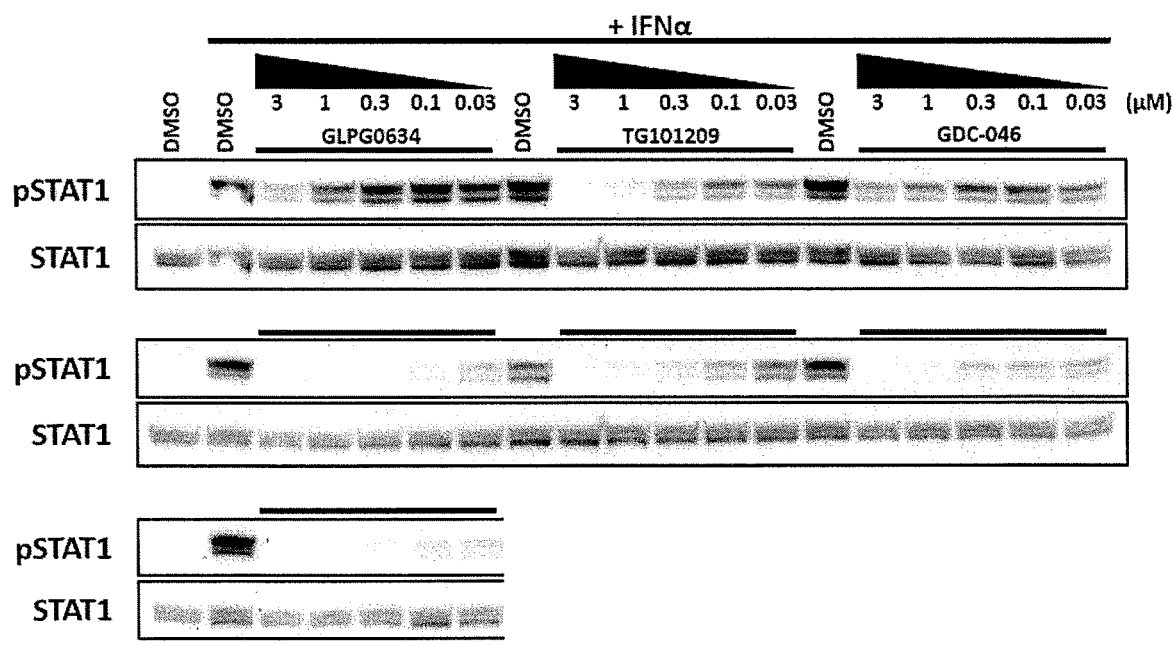
Figure 1C:
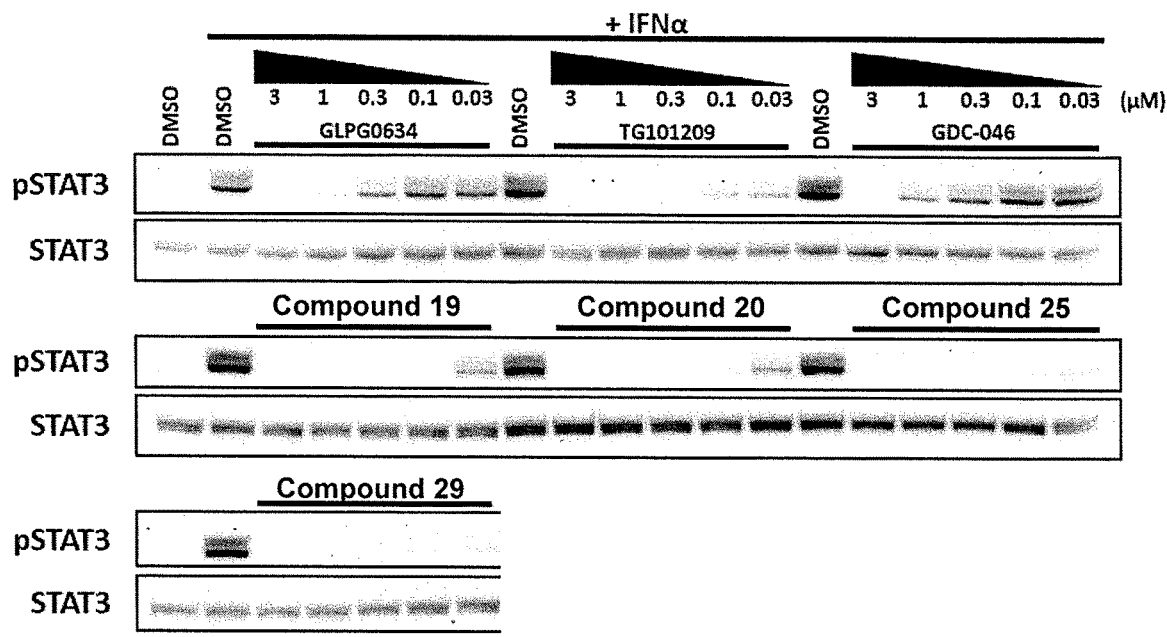
Figure 1D:
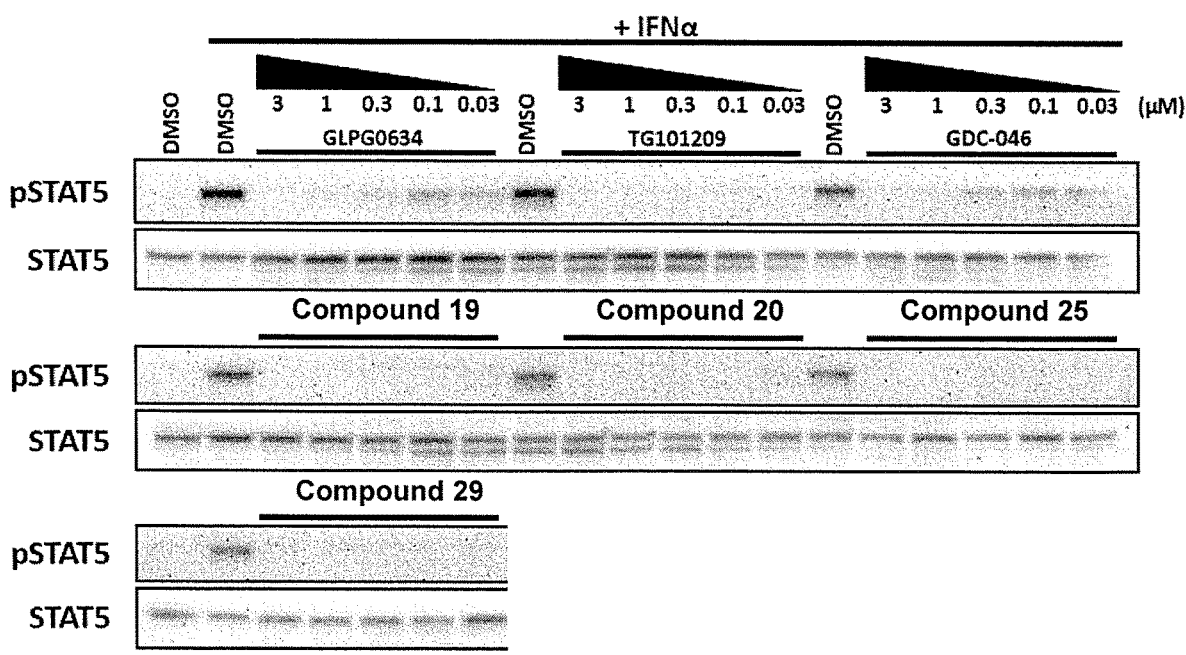
Figure 1E:
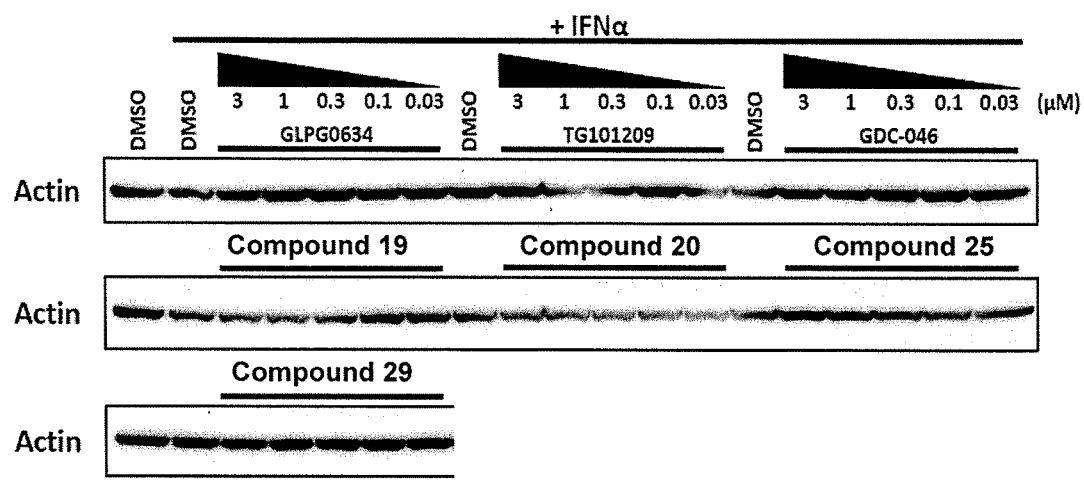

The invention will now be illustrated, but not limited, by reference to the specific embodiments described in the following examples.

Example 1

Enzyme Inhibition

Compounds of the invention were assayed for their ability to inhibit TYK2 kinase and other JAK kinases.

Substrates and kinases used in the assays are identified in Table 2 below.

Kinase assays were performed at Reaction Biology Corp., Malvern, Pa., USA, using the following general procedure:

1) Prepare indicated substrate in freshly prepared Base Reaction Buffer (20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, 1% DMSO).
2) Deliver cofactors (1.5 mM $CaCl_2$, 16 ug/mL Calmodulin, 2 mM $MnCl_2$) to the substrate solution above
3) Deliver indicated kinase into the substrate solution and gently mix
4) Deliver varying concentrations of test compound in DMSO into the kinase reaction mixture
5) Deliver $^{33}$P-ATP (specific activity 0.01 μCi/μL final) into the reaction mixture to initiate the reaction
6) Incubate kinase reaction for 120 min at room temperature
7) Reactions are spotted onto P81 ion exchange filter paper (Whatman #3698-915)
8) Unbound phosphate is removed by washing filters extensively in 0.75% Phosphoric acid.
9) $^{33}$P signal was determined using Typhoon phosphorimagers (GE Healthcare). After subtraction of background derived from control reactions containing inactive enzyme, $IC_{50}$ values were determined using the nonlinear regression function in Prism (Graphpad software).

TABLE 2

| Protein Name | HUGO symbol | Substrate | Genbank Accession # | Protein Accession # | Clone | Expression | Tag |
|---|---|---|---|---|---|---|---|
| JAK1 | JAK1 | pEY | NP_002218.2 | P23458 | aa 866-1154 | Baculovirus in Sf21 insect cells | N-terminal GST tag |
| JAK2 | JAK2 | pEY | NP_004963 | O60674 | aa 809-1132 + g | Baculovirus in Sf21 insect cells | N-terminal GST tag |
| JAK3 | JAK3 | JAK3tide | NP_000206 | P52333 | aa 781-1124 | Baculovirus in Sf21 insect cells | N-terminal GST tag |
| TYK2 | TYK2 | AXLtide | NP_003322.2 | P29597 | Aa 833-1187 | Baculovirus in Sf21 insect cells | N-terminal GST tag |

Substrates:
AXLtide=[KKSRGDYMTMQIG]
JAK3tide=[Ac-GEEEEYFELVKKKK-$NH_2$]
pEY=poly Glu-Tyr [Glu:Tyr (4:1), M.W.=5,000-20,000]

The results are shown in Table 3 below.

TABLE 3

| Compound Number (and method of preparation) | STRUCTURE | In Vitro Enzyme $IC_{50}$ (nM) | | | |
|---|---|---|---|---|---|
| | | TYK2 | JAK1 | JAK2 | JAK3 |
| Compound 1 (Example Q-3 in WO2008/139161) | 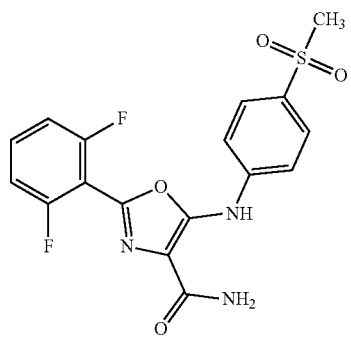 [SMILES: CS(=O)(=O)c1ccc(Nc2oc(-c3c(F)cccc3F)nc2C(N)=O)cc1] | 13.5 | 90.2 | 234.7 | 404.8 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 2 (Example Q-25 in WO2008/139161) | 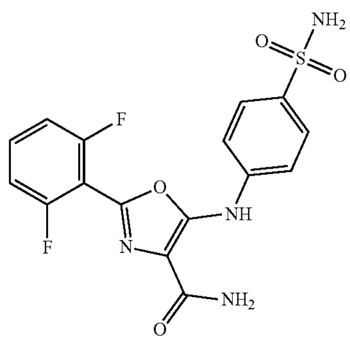 | 14.6 | 78.2 | 146.6 | 418.8 |
| Compound 3 (Example Q-26 in WO2008/139161) | 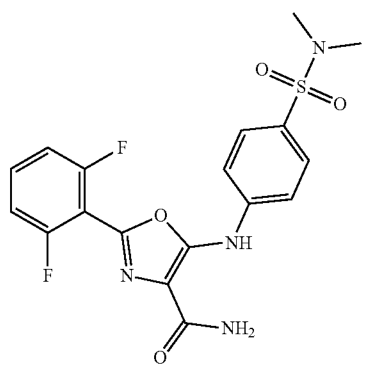 [SMILES: CN(C)S(=O)(=O)c1ccc(Nc2oc(-c3c(F)cccc3F)nc2C(N)=O)cc1] | 5.3 | 47.6 | 95.0 | 359.0 |
| Compound 4 (Example Q-27 in WO2008/139161) | 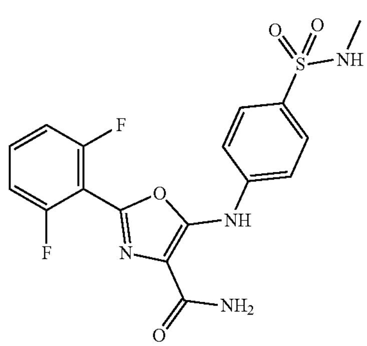 [SMILES: CNS(=O)(=O)c1ccc(Nc2oc(-c3c(F)cccc3F)nc2C(N)=O)cc1] | 13.8 | 65.6 | 109.0 | 387.2 |
| Compound 5 (Example Q-20 in WO2008/139161) | 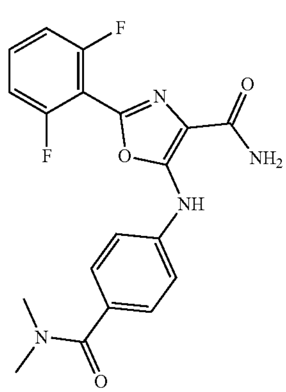 [SMILES: CN(C)C(=O)c1ccc(Nc2oc(-c3c(F)cccc3F)nc2C(N)=O)cc1] | 9.2 | 88.6 | 112.1 | 218.9 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 6 (Example Q-51 in WO2008/139161) | 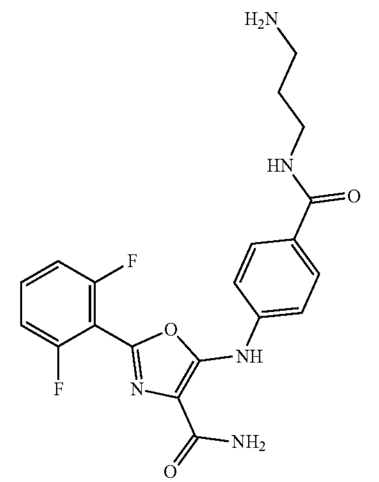 [SMILES: NCCCNC(=O)c1ccc(Nc2oc(-c3c(F)cccc3F)nc2C(N)=O)cc1] | 25.0 | 192.4 | 297.1 | 471.6 |
| Compound 7 (Example Q-54 in WO2008/139161) | 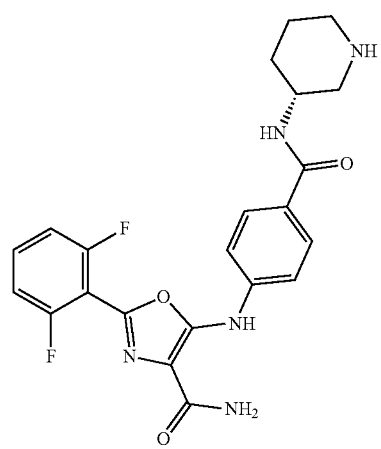 [SMILES: NC(=O)c1nc(-c2c(F)cccc2F)oc1Nc1ccc(C(=O)N[C@@H]2CCCNC2)cc1] | 9.8 | 201.5 | 261.0 | 419.3 |
| Compound 8 (Example Q-53 in WO2008/139161) | 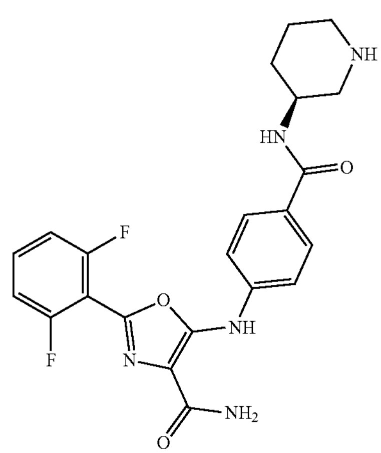 [SMILES: NC(=O)c1nc(-c2c(F)cccc2F)oc1Nc1ccc(C(=O)N[C@H]2CCCNC2)cc1] | 12.9 | 201.0 | 267.5 | 408.5 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 9 (Example U-2 in WO2008/139161) | 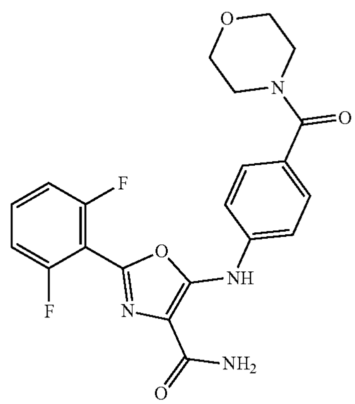 [SMILES: NC(=O)c1nc(-c2c(F)cccc2F)oc1Nc1ccc(C(=O)N2CCOCC2)cc1] | 22.7 | 75.6 | 267.4 | 423.4 |
| Compound 10 (Example U-3 in WO2008/139161) | 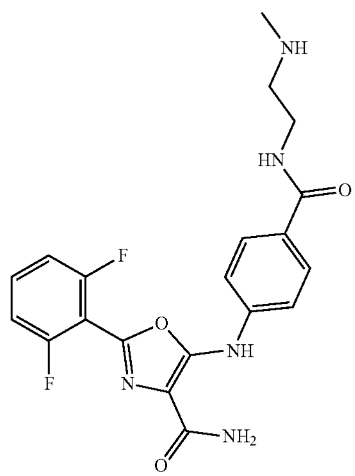 [SMILES: CNCCNC(=O)c1ccc(Nc2oc(-c3c(F)cccc3F)nc2C(N)=O)cc1] | 20.5 | 183.3 | 311.4 | 397.2 |
| Compound 11 (Example U-4 in WO2008/139161) | 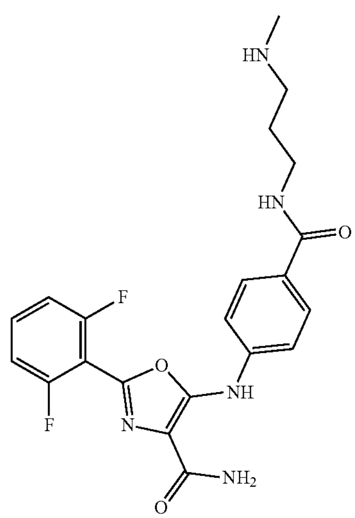 [SMILES: CNCCCNC(=O)c1ccc(Nc2oc(-c3c(F)cccc3F)nc2C(N)=O)cc1] | 15.1 | 189.6 | 338.4 | 387.7 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 12 (Example U-6 in WO2008/139161) | 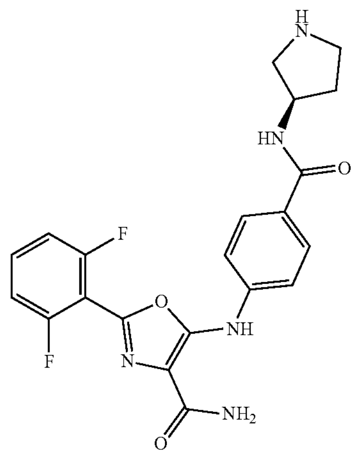 [SMILES: NC(=O)c1nc(-c2c(F)cccc2F)oc1Nc1ccc(C(=O)N[C@@H]2CCNC2)cc1] | 23.41 | 168.6 | 292.4 | 346.2 |
| Compound 13 (Example U-7 in WO2008/139161) | 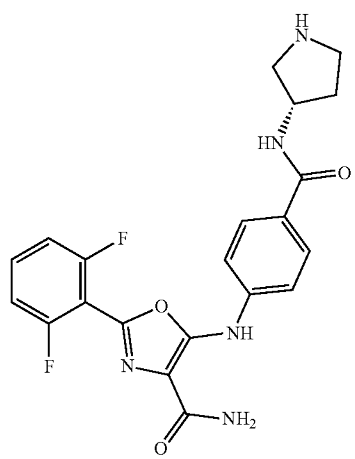 [SMILES: NC(=O)c1nc(-c2c(F)cccc2F)oc1Nc1ccc(C(=O)N[C@H]2CCNC2)cc1] | 11.2 | 123.0 | 181.6 | 341.5 |
| Compound 14 (Example U-12 in WO2008/139161) | 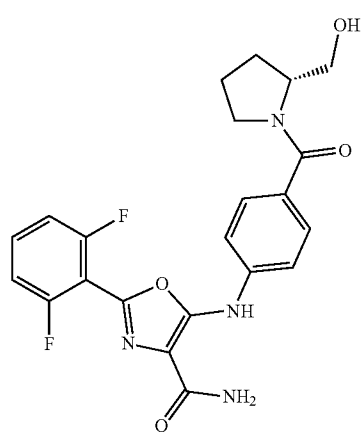 [SMILES: NC(=O)c1nc(-c2c(F)cccc2F)oc1Nc1ccc(C(=O)N2CCC[C@@H]2CO)cc1] | 9.6 | 67.22 | 36.0 | 125.9 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 15 (Example U-16 in WO2008/139161) | 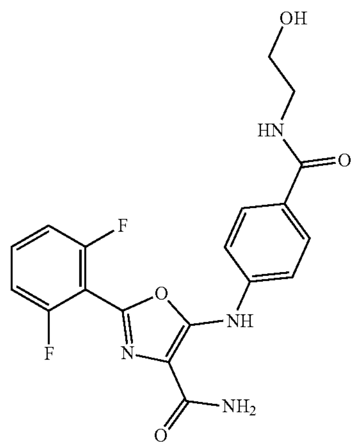 [SMILES: NC(=O)c1nc(-c2c(F)cccc2F)oc1Nc1ccc(C(=O)NCCO)cc1] | 7.5 | 41.1 | 101.3 | 194.9 |
| Compound 16 (Example U-17 in WO2008/139161) | 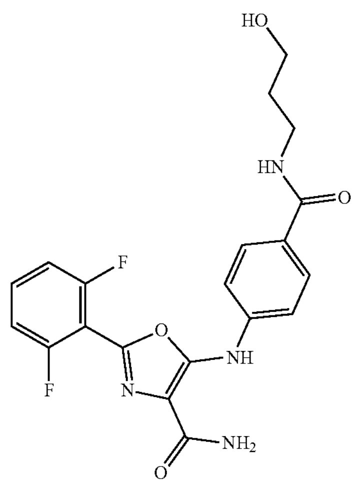 [SMILES: NC(=O)c1nc(-c2c(F)cccc2F)oc1Nc1ccc(C(=O)NCCCO)cc1] | 8.4 | 58.1 | 118.8 | 199.1 |
| Compound 17 (Example U-21 in WO2008/139161) | 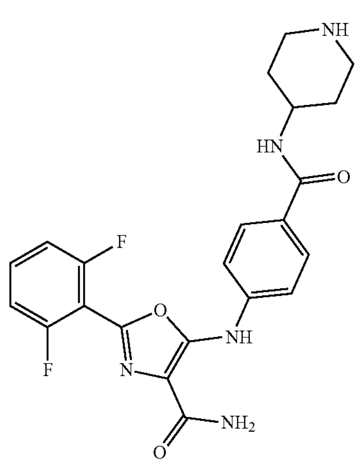 [SMILES: NC(=O)c1nc(-c2c(F)cccc2F)oc1Nc1ccc(C(=O)NC2CCNCC2)cc1] | 13.7 | 152.8 | 167.2 | 99.2 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 18 (Example U-18 in WO2008/139161) | 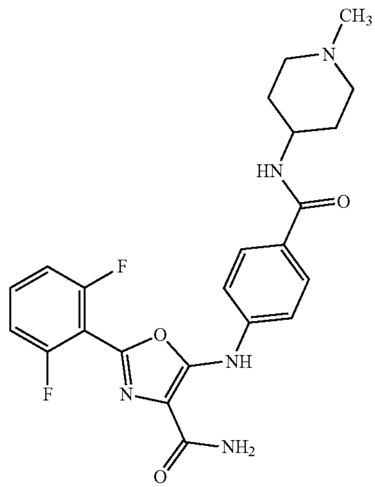 [SMILES: CN1CCC(NC(=O)c2ccc(Nc3oc(-c4c(F)cccc4F)nc3C(N)=O)cc2)CC1] | 13.8 | 118.3 | 191.8 | 164.6 |
| Compound 19 Example 19 in WO2015/032423 | 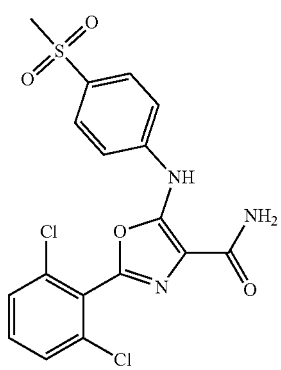 [SMILES: CS(=O)(=O)c1ccc(Nc2oc(-c3c(Cl)cccc3Cl)nc2C(N)=O)cc1] | 2.3 | 21.9 | 87.7 | 214 |
| Compound 20 Example 20 in WO2015/032423 | 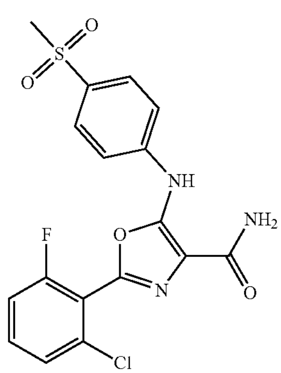 [SMILES: CS(=O)(=O)c1ccc(Nc2oc(-c3c(F)cccc3Cl)nc2C(N)=O)cc1] | 2.7 | 28.7 | 72.6 | 165 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 21 Example 21 in WO2015/032423 | 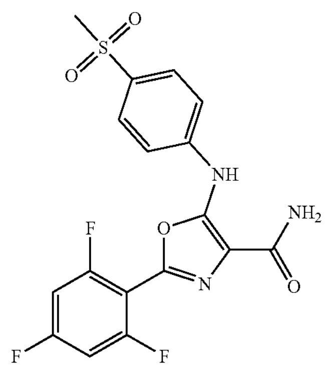 [SMILES: CS(=O)(=O)c1ccc(Nc2oc(-c3c(F)cc(F)cc3F)nc2C(N)=O)cc1] | 68.3 | 241 | 412 | 2180 |
| Compound 22 Example 22 in WO2015/032423 | 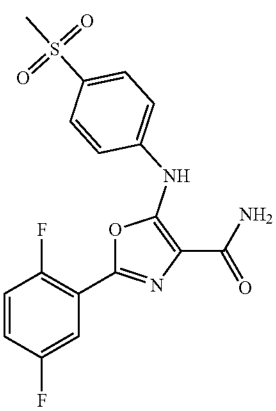 [SMILES: CS(=O)(=O)c1ccc(Nc2oc(-c3cc(F)ccc3F)nc2C(N)=O)cc1] | 183 | 843 | 663 | 5500 |
| Compound 23 Example 23 in WO2015/032423 | 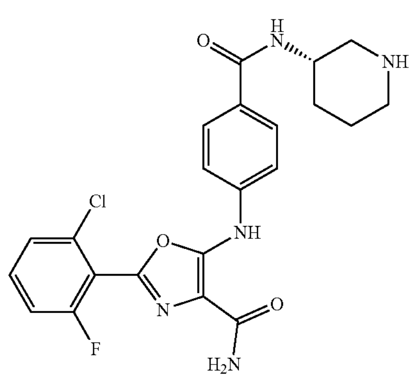 [SMILES: NC(=O)c1nc(-c2c(F)cccc2Cl)oc1Nc1ccc(C(=O)N[C@H]2CCCNC2)cc1] | 1.89 | 63.3 | 61.9 | 240 |
| Compound 24 Example 24 in WO2015/032423 | 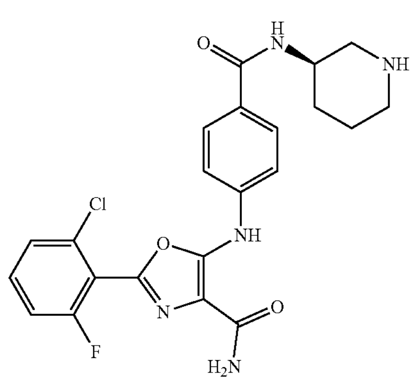 [SMILES: NC(=O)c1nc(-c2c(F)cccc2Cl)oc1Nc1ccc(C(=O)N[C@@H]2CCCNC2)cc1] | 5.11 | 157 | 125 | 167 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 25 Example 25 in WO2015/032423 | 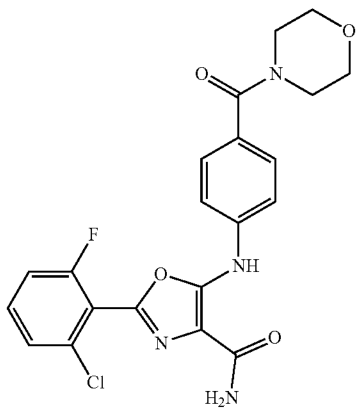 [SMILES: NC(=O)c1nc(-c2c(F)cccc2Cl)oc1Nc1ccc(C(=O)N2CCOCC2)cc1] | 0.564 | 28.9 | 30.9 | 43.2 |
| Compound 26 Example 26 in WO2015/032423 | 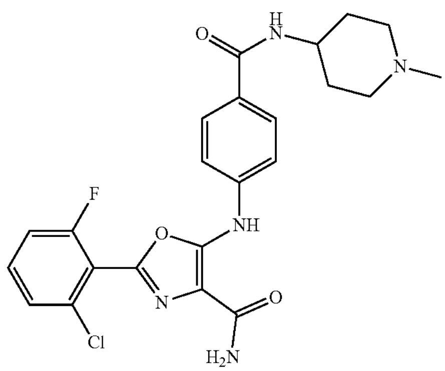 [SMILES: CN1CCC(NC(=O)c2ccc(Nc3oc(-c4c(F)cccc4Cl)nc3C(N)=O)cc2)CC1] | 2.98 | 100 | 87.8 | 132 |
| Compound 27 Example 27 in WO2015/032423 | 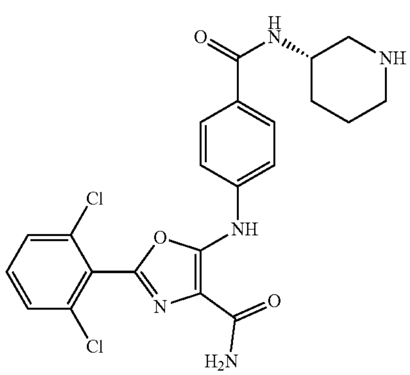 [SMILES: NC(=O)c1nc(-c2c(Cl)cccc2Cl)oc1Nc1ccc(C(=O)N[C@H]2CCCNC2)cc1] | 1.21 | 72.2 | 93.3 | 233 |
| Compound 28 Example 28 in WO2015/032423 | 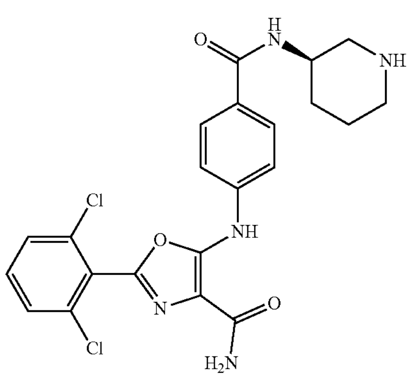 [SMILES: NC(=O)c1nc(-c2c(Cl)cccc2Cl)oc1Nc1ccc(C(=O)N[C@@H]2CCCNC2)cc1] | 1.77 | 108 | 122 | 194 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 29 Example 29 in WO2015/032423 | 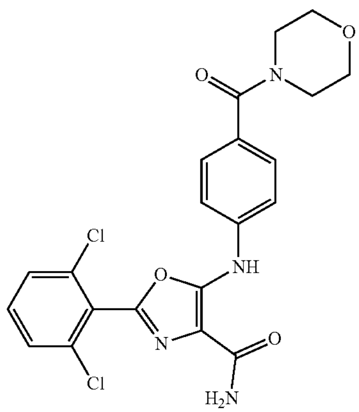 [SMILES: NC(=O)c1nc(-c2c(Cl)cccc2Cl)oc1Nc1ccc(C(=O)N2CCOCC2)cc1] | 0.617 | 16.8 | 40.3 | 90.8 |
| Compound 30 Example 30 in WO2015/032423 | 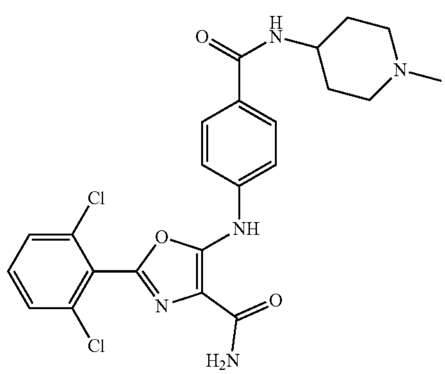 [SMILES: CN1CCC(NC(=O)c2ccc(Nc3oc(-c4c(Cl)cccc4Cl)nc3C(N)=O)cc2)CC1] | 1.52 | 83.4 | 106 | 164 |
| Compound 31 Example 31 in WO2015/032423 | 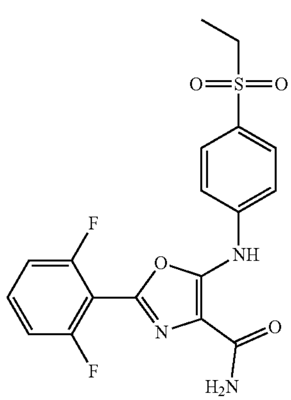 [SMILES: CCS(=O)(=O)c1ccc(Nc2oc(-c3c(F)cccc3F)nc2C(N)=O)cc1] | 4.41 | 222 | 213 | 390 |

TABLE 3-continued

| Compound Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Compound 32 Example 32 in WO2015/032423 | 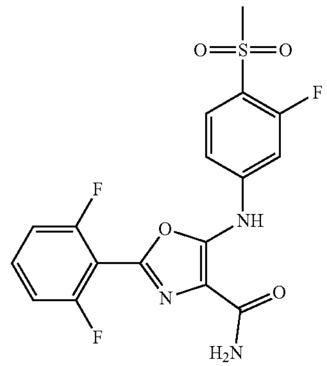 [SMILES: CS(=O)(=O)c1ccc(Nc2oc(-c3c(F)cccc3F)nc2C(N)=O)cc1F] | 31 | 1970 | 1590 | 5370 |
| Compound 33 Example 33 in WO2015/032423 | 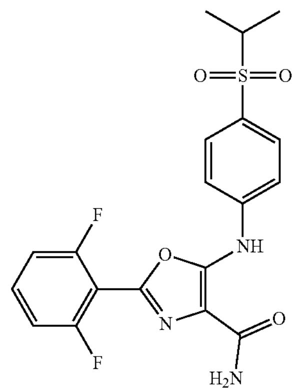 [SMILES: CC(C)S(=O)(=O)c1ccc(Nc2oc(-c3c(F)cccc3F)nc2C(N)=O)cc1] | 5.47 | 135 | 153 | 516 |

Example 2

Cell Proliferation Assay

Compounds 19, 20, 25 and 29 were investigated in a panel of five cell lines:
Jurkat
MOLT-4
CCRF-CEM
Loucy
CCRF-HSB-2

Jurkat, MOLT-4, CCRF-CEM and CCRF-HSB-2 cells are all TYK2-dependent T-ALL cells.

Loucy cells are TYK2-independent T-ALL cell lines.

Dexamethasone, Etoposide and Paclitaxel were used as positive controls.

Compound effects were studied 7 days after compound addition

Protocol

Cells were seeded in 384-well plates at the appropriate density and allowed to adhere overnight prior to addition of compound or vehicle control.

Compounds 19, 20, 25 and 29 were prepared from DMSO stocks to give a final concentration range of between approximately 3 nM and 30 µM. The final DMSO concentration was constant at 0.15%.

Test compounds were incubated with the cells for 7 days at 37° C. 5% CO$_2$ in a humidified atmosphere.

A volume of ATPlite reagent, equal to the volume of cell culture medium present in each well, was then added and plates were shaken at room temperature (RT) for 2 min, and incubated at RT for a further 10 min. Luminescent product was detected using a BMG FLUOstar plate reader.

The data were analysed using a 4-parameter logistic equation in GraphPad Prism.

The results are shown in Table 5 below.

TABLE 5

| | Cell Proliferation IC$_{50}$ (µM) | | | | |
|---|---|---|---|---|---|
| Compound Number | Jurkat | MOLT-4 | CCRF-CEM | Loucy | CCRF-HSB-2 |
| Compound 19 | 8% inh. @ 30 µM | 12 | 34% inh. @ 30 µM | 20 | 17 |
| Compound 20 | 2.1 | 3.1 | 8.9 | 3.9 | 2.8 |
| Compound 25 | 0.15 | 0.27 | 0.38 | 0.35 | 0.43 |
| Compound 29 | 0.6 | 1.2 | 1.8 | 1.7 | 1.4 |
| Etoposide | 94 | 7.7 | 17 | 33 | 4.7 |
| Dexamethasone | 5% inh. @ 10 µM | 21% inh. @ 10 µM | 59 | 25% inh. @ 10 µM | 49 |
| Paclitaxel | 1.8 | 0.66 | 4.4 | 2.2 | 1.3 |

Example 3

Western Blot Assay—Short Term Compound Treatment

Jurkat cells were treated with Compounds 19, 20, 25 and 29 (of Example 1) and three benchmark inhibitors (GLPG0634 (Filgotinib, developed by Galapagos), TG101209 and GDC-046) as comparative examples using the protocol set out below.

Cells were incubated with compounds at five concentrations (3, 1, 0.3, 0.1 & 0.03 µM) for 1 hr, then stimulated with INFα for 20 m, before cells were harvested.

Cell lysates were analysed by Western blot and then probed with antibodies against the following:
phospho-TYK2/total-TYK2
phospho-STAT1/total-STAT1
phospho-STAT3/total-STAT3
phospho-STAT5/total-STAT5
Actin The details of the antibodies are set out in the table below.

| Antigen | Size (kDa) | Supplier | Cat. No. | Dilution | Incubation/ Block Conditions | Secondary |
|---|---|---|---|---|---|---|
| TYK2 | 134 | Cell Signalling | 9312 | 1:500 | o/n 4° C. 5% BSA | Anti-Rabbit |
| pTYK2 (Tyr1054/1055) | 134 | Cell Signalling | 9321 | 1:500 | o/n 4° C. 5% BSA | Anti-Rabbit |
| JAK1 | 130 | Cell Signalling | 3344 | 1:5000 | o/n 4° C. 5% BSA | Anti-Rabbit |
| pJAK1 (Tyr1022/1023) | 130 | Cell Signalling | 3331 | 1:500 | o/n 4° C. 5% BSA | Anti-Rabbit |
| JAK2 | 125 | Cell Signalling | 3230 | 1:1000 | o/n 4° C. 5% BSA | Anti-Rabbit |
| pJAK2 (Tyr1022/1023) | 125 | Cell Signalling | 3776 | 1:1000 | o/n 4° C. 5% BSA | Anti-Rabbit |
| STAT1 | 84/91 | Cell Signalling | 9175 | 1:500 | o/n 4° C. 5% BSA | Anti-Rabbit |
| pSTAT1 (Tyr701) | 84/91 | Cell Signalling | 7649 | 1:500 | o/n 4° C. 5% BSA | Anti-Rabbit |
| STAT3 | 79/86 | Cell Signalling | 12640 | 1:3000 | o/n 4° C. 5% BSA | Anti-Rabbit |
| pSTAT3 (Tyr705) | 79/86 | Cell Signalling | 9145 | 1:2000 | o/n 4° C. 5% BSA | Anti-Rabbit |
| STAT5 | 90 | Cell Signalling | 9363 | 1:500 | o/n 4° C. 5% BSA | Anti-Rabbit |
| pSTAT5 (Tyr694) | 90 | Cell Signalling | 4322 | 1:1000 | o/n 4° C. 5% BSA | Anti-Rabbit |
| Beta Actin | 45 | Sigma | A5441 | 1:200,000 | o/n 4° C. 5% Milk | Anti-Mouse |

Protocol

Cell were plated in 6-well plates at $2.5 \times 10^6$ cells per well in 2 ml of media (RPMI+10% FBS) and incubated for at least 1 h at 37° C., 5% $CO_2$.

Cells were treated with the indicated concentrations of compounds for 1 hrs.

Cells were then stimulated with IFNα (6000 U/ml) for 20 min at 37° C., 5% $CO_2$.

Cells were harvested by centrifuging at 12,000 rpm for 1 min (4° C.), washed in ice cold PBS and centrifuged again at 12,000 rpm for 1 min (4° C.).

The supernatant was removed and the cell pellet snap frozen on dry ice.

Cells were lysed in RIPA buffer (with protease and phosphatase inhibitors) and incubated on ice for 30 min.

Cellular debris was pelleted at 13,000 rpm for 5 min at 4° C., supernatant was transferred to a fresh tube.

Protein concentration was estimated using a BCA assay.

50 µg of protein was loaded onto 4-12% NuPAGE Novex Bis-Tris protein gels (MOPs buffer).

Protein was transferred to a PVDF membrane using dry transfer (iBlot) and western blotting performed against the antigens of interest.

Results

The Western Blot analyses are shown in FIGS. 1A to 1E.

An increase in TYK2 activation loop phosphorylation (Tyr1054/1055) was observed following compound exposure (FIG. 1A), a phenomenon that has been previously observed with other ATP-competitive JAK family inhibitors (see for example Andraos, R. et al., "Modulation of Activation-Loop Phosphorylation by JAK Inhibitors is Binding Mode Dependent", Cancer Discovery, June 2012, 513) suggesting that compounds are interacting at the ATP-binding site of TYK2. A dose-dependent suppression of STAT1, STAT3 and STAT5 phosphorylation was also observed (FIG. 1B-C), consistent with TYK2 inhibition.

Example 4

Western Blot Assay—Chronic Compound Treatment

MOLT-4 cells were treated with Compounds 25 and 29 (of Example 1) and three benchmark inhibitors (GLPG0634 (Filgotinib, developed by Galapagos), TG101209 and GDC-046) as comparative examples at five concentrations (3, 1, 0.3, 0.1 and 0.03 µM), for 48 hrs.

Cell lysates were analysed by Western blot and probed with antibodies against PARP and Actin.

The details of the antibodies used are set out in the table below.

| Antigen | Size (kDa) | Supplier | Cat. No. | Dilution | Incubation/ Block Conditions | Secondary |
|---|---|---|---|---|---|---|
| PARP | 116/89 | Cell Signalling | 9542 | 1:2,000 | o/n 4° C. 5% Milk | Anti-Rabbit |
| Beta Actin | 45 | Sigma | A5441 | 1:200,000 | o/n 4° C. 5% Milk | Anti-Mouse |

Protocol

Cell were plated in 6-well plates at 4e6 cells per well in 6 ml of media (RPMI+10% FBS) and incubated for at least 1 h at 37° C., 5% $CO_2$.

Cells were treated with the indicated concentrations of compounds for 48 hrs.

Cells were harvested by centrifuging at 12,000 rpm for 1 min (4° C.), washed in ice cold PBS and centrifuged again at 12,000 rpm for 1 min (4° C.).

The supernatant was removed and the cell pellet snap frozen on dry ice.

Cells were lysed in RIPA buffer (with protease and phosphatase inhibitors) and incubated on ice for 30 min.

Cellular debris was pelleted at 13,000 rpm for 5 min at 4° C., supernatant was transferred to a fresh tube.

Protein concentration was estimated using a BCA assay.

30 μg of protein was loaded onto 4-12% NuPAGE Novex Bis-Tris protein gels (MOPs buffer).

Protein was transferred to a PVDF membrane using dry transfer (iBlot) and western blotting performed against the antigens of interest.

Results

Figure 2:
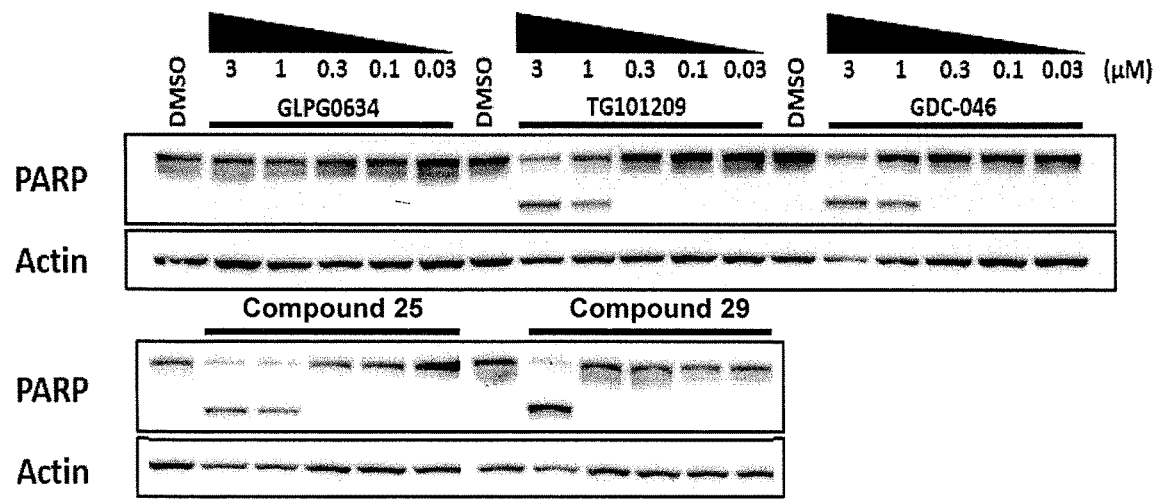
FIG. 2 shows a Western blot analysis of cell lysates obtained by incubating MOLT-4 cells with Compounds 25 and 29 and three benchmark inhibitors (GLPG0634 (Filgotinib, developed by Galapagos), TG101209 and GDC-046) as comparative examples and then probing with antibodies against PARP and Actin.

Western blot analysis is shown in FIG. 2.

The presence of cleaved PARP at concentrations ≥1 μM (Compound 25) and ≥3 μM (Compound 29) shows that compounds cause apoptosis of MOLT-4 cells at such concentrations, and that the anti-proliferative effects of the compounds are therefore likely due to induction of apoptosis, rather than due to affecting progress through the cell-cycle.

Example 5

Western Blot in CCRF-HSB-2 Cell Line

CCRF-HSB-2 cells show constitutive phosphorylation of STAT1, STAT3 and STAT5 in the absence of IFNα stimulation by Western blot. Cells were treated with Compounds 25 and 29 for 48 h before being harvested.

Cell lysates were analysed by Western blot and probed with antibodies against the following:
phospho-TYK2 & total-TYK2
phospho-STATs 1/3/5 & total-STATs 1/3/5
Bcl-2
PARP Protocol CCRF-HSB-2 cells were plated in 6-well plates at 5e6 cells per well in 10 ml of media (IMDM+10% FBS) and incubated for at least 1 h at 37° C., 5% CO2.

Cells were treated with the indicated concentrations of compounds for 48 hrs.

Cells were harvested by centrifuging at 12,000 rpm for 1 min (4° C.), washed in ice cold PBS and centrifuged again at 12,000 rpm for 1 min (4° C.).

The supernatant was removed and the cell pellet snap frozen on dry ice.

Cells were lysed in RIPA buffer (with protease and phosphatase inhibitors) and incubated on ice for 30 min.

Cellular debris was pelleted at 13,000 rpm for 5 min at 4° C., supernatant was transferred to a fresh tube.

Protein concentration was estimated using a BCA assay.

25 μg of protein was loaded onto 4-12% NuPAGE Novex Bis-Tris protein gels (MOPs buffer).

Protein was transferred to a PVDF membrane using dry transfer (iBlot) and western blotting performed against the antigens of interest.

Results

Figure 3:
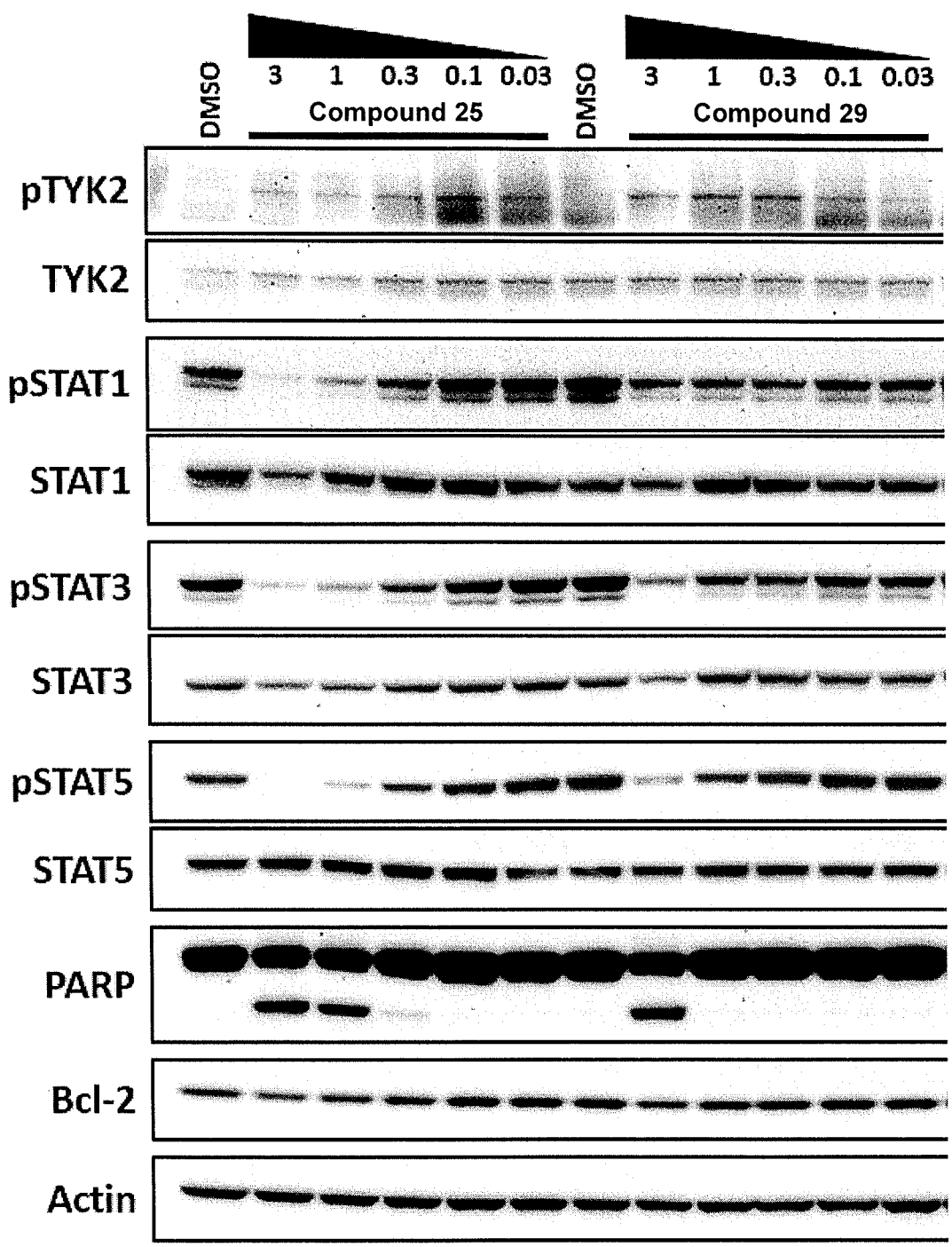
FIG. 3 shows a Western blot analysis of cell lysates obtained by incubating CCRF-HSB-2 cells with Compounds 25 and 29 and then probing with antibodies against phospho-TYK2 & total-TYK2, phospho-STATs 1/3/5 & total-STATs 1/3/5, BCL2 and PARP.

Western blot analysis is shown in FIG. 3. The Western blots show dose responsive reduction in the phosporylated signals, induction of cleaved Parp and reduction in levels of the anti-apoptotic protein, BCL-2 consistent with TYK2 inhibition having an anti-proliferative effect in T-ALL cell lines through apoptosis caused by reductions in BCL-2 levels Example 6

PKPD Study in Male SCID Mice Bearing MOLT-4-Tumours

Male SCID mice were implanted with MOLT-4 tumour cells ($1 \times 10^7$ in 50% matrigel). When tumours reached approximately 150 $mm^3$ animals received a single dose of test compound. Animals to be sampled at 24 hrs also received a second dose at 12 hrs.

At 1, 6 and 24 h animals were sacrificed and plasma prepared. Tumour tissue was removed and divided into 2 sections—one for bioanalysis and the second for homogenisation for western blotting.

Tumour tissue was homogenised in lysis buffer supplemented with protease and phosphatase inhibitors. Protein in individual samples was quantified using a commercially available BCA kit.

Figure 4:
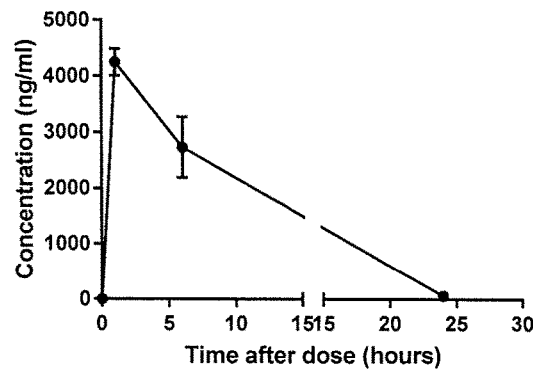
FIG. 4 is a plot of plasma concentrations of Compound 25 against time after dose in male SCID mice implanted with MOLT-4 tumour cells.
Figure 5:
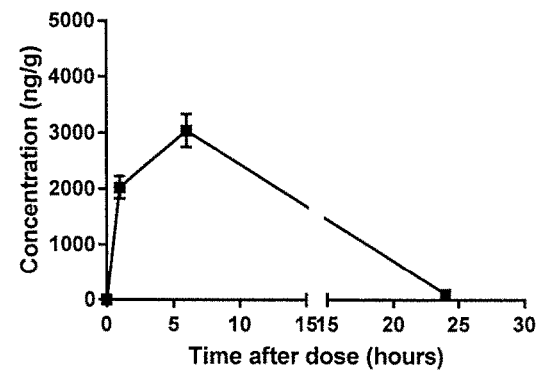
FIG. 5 is a plot of tumour concentrations of Compound 25 against time after dose in male SCID mice implanted with MOLT-4 tumour cells.

50 μg total protein was run on a 4-20% pre-cast gel and transferred to PVDF membrane before being incubated with the following antibodies:
pSTAT1
STAT1
pTYK2
TYK2
Cleaved PARP
B-actin
Anti-rabbit IgG Results Pharmacokinetic analysis of plasma showed a maximal exposure of Compound 25 one hour after dosing, with a maximal concentration >4000 ng/mL (FIG. 4). Pharmacokinetic analysis of tumour tissue showed a maximal exposure of Compound 25 six hours after dosing, with a maximal concentration >3000 ng per gram of tumour tissue (FIG. 5).

Figure 6:
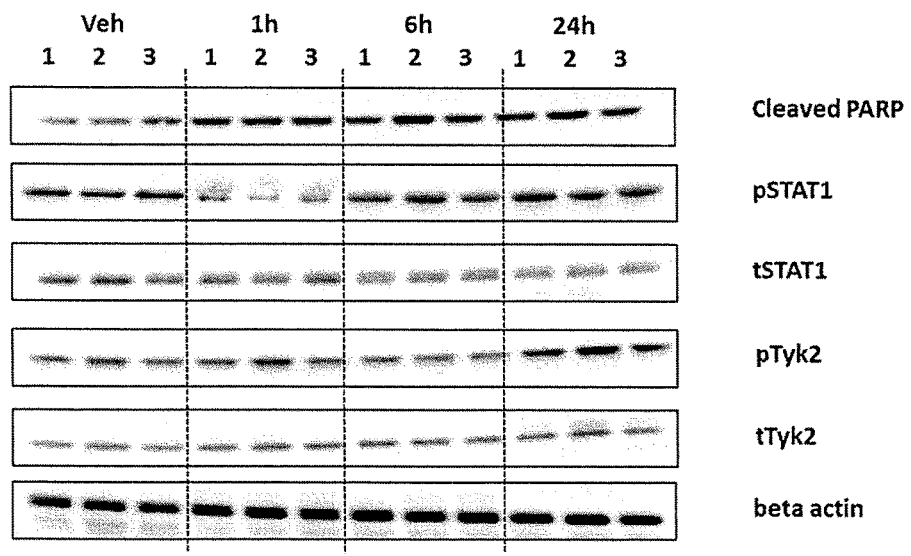
FIG. 6 shows a Western blot analysis for levels of phosphorylated STAT1 and phosphorylated TYK2 in homogenised extracts from the tumour tissues of male SCID mice implanted with MOLT-4 tumour cells and subsequently treated with Compound 25 after tumour development.
Figure 7:
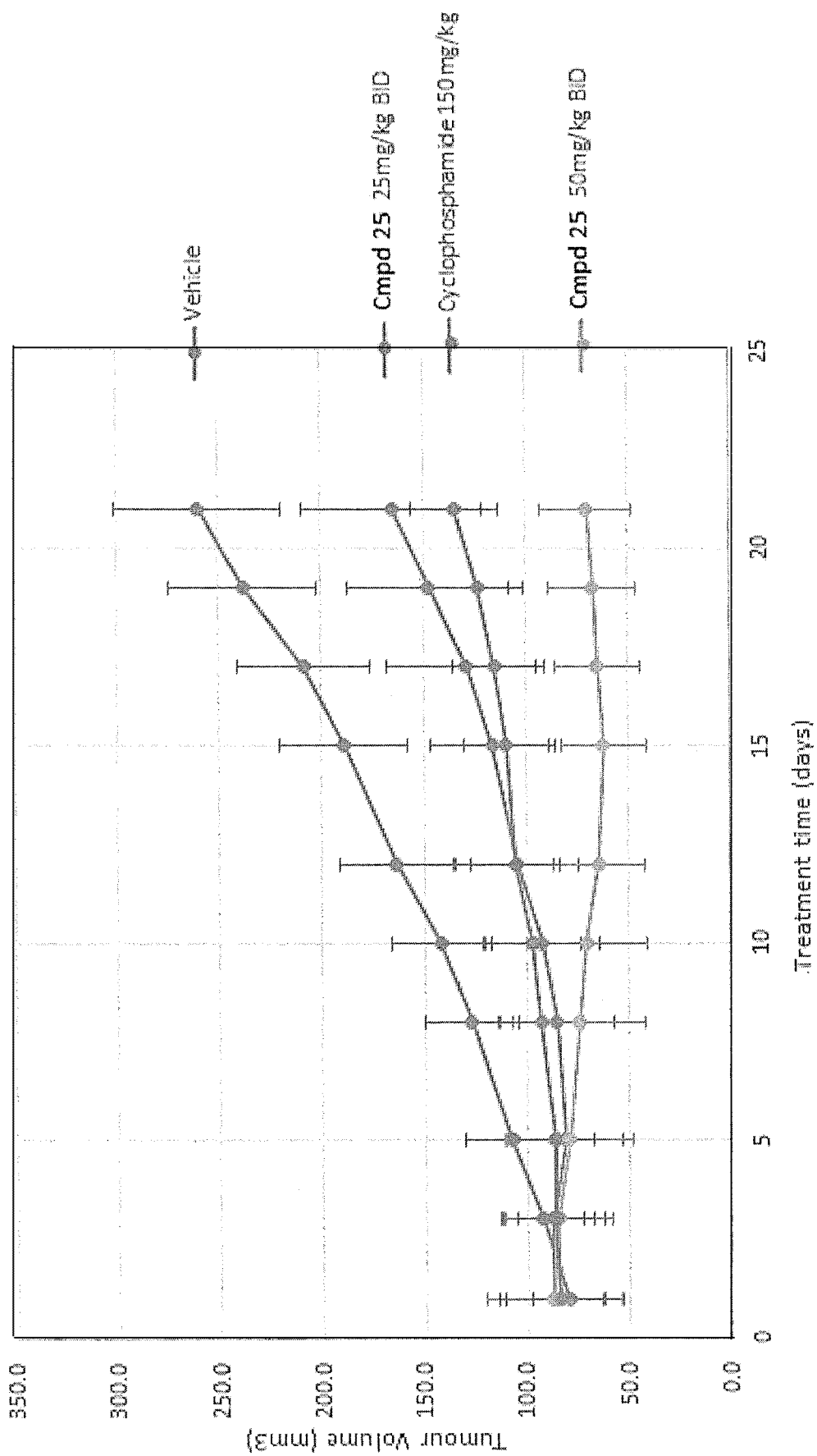
FIG. 7 is a plot of tumour volume against treatment time for male SCID mice bearing MOLT-4 tumours and treated with Compound 25 or cyclophosphamide.

Western blot analysis (FIG. 6) shows a reduction in level of phosphorylated STAT1 at t=1 h, returning to normal in comparison with vehicle treated controls between 6 and 24 h. An increase in cleaved Parp, relative to vehicle treated controls, was observed between 1 and 24 h in animals dosed with compound 25. Phosphorylated TYK2 levels were increased at 24 h following the initial dose. The data are consistent with Compound 25 interacting at the ATP binding site of TYK2, leading to a reduction in phosphorylated STAT1 and increased apoptosis.

Example 7

Efficacy Study in Male SCID Mice Bearing MOLT-4 Tumours

MOLT-4 cells ($1\times10^7$ in matrigel) were implanted onto the rear dorsum of male SCID mice using a 25-gauge needle. When tumours reached approximately 100 mm³ the mice were randomly assigned to the following treatment groups.

Treatment Groups:

| Group | Drug | Dose | Schedule | No of animals | Dosing solution |
|---|---|---|---|---|---|
| 1 | Vehicle only | — | BID | 10 | — |
| 2 | Cyclophosphamide | 150 mg/kg | Q5D | 10 | 15 mg/ml |
| 3 | Compound 25 | 25 mg/kg | BID | 10 | 2.5 mg/ml |
| 4 | Compound 25 | 50 mg/kg | BID | 10 | 5 mg/ml |

Compound 25 was dosed twice daily per os for 21 days. Tumours in vehicle-treated animals grew steadily during the study. Compound 25 demonstrated good efficacy in controlling MOLT-4 tumour growth. A dose response was observed following treatment with Compound 25 with 50 mg/kg resulting in tumour regression and 25 mg/kg slowing growth but not resulting in tumour regression. At the end of the study period T/C (test versus control) values were 63.5% for Compound 25 at 25 mg/kg, and 27.0% at 50 mg/kg and 51.7% for cyclophosphamide. At day 21 tumour volume was significantly smaller in all treatment groups than those observed in animals treated with vehicle only (p<0.0001 in all cases, ANOVA with Tukey post-hoc test).

At the end of the study tumour tissue was resected and weighed. Tumour weights followed a similar pattern to tumour volume. T/C (test versus control) values were 60.7% for Compound 25 at 25 mg/kg, 24.0% at 50 mg/kg, and 49.0% for cyclophosphamide. At day 21 tumour weight was significantly smaller in all treatment groups than those observed in animals treated with vehicle only (p<0.0001 in all cases, ANOVA with Tukey post-hoc test).

Example 8

Tumour Growth Delay Study in Male SCID Mice Bearing CCRF-HSB-2 Tumours

A total of 40 male SCID mice aged 5-7 weeks were used for the study. These were purchased from Charles River and allowed to acclimatize for 7 days prior to tumour implantation. Animals were housed in IVC cages (up to 5 per cage) with individual mice identified by tail mark. All animals were allowed free access to a standard certified commercial diet and sanitised water during the study. The holding room was maintained under standard conditions: 20-24° C., 40-70% humidity and a 12 h light/dark cycle.

CCRF-HSB-2 cells ($5\times10^6$ in matrigel) were implanted onto the rear dorsum of male SCID mice using a 25-gauge needle. When tumours reached a size of approximately 100-150 mm³ the mice were randomly assigned to the following treatment groups.

| Group | Drug | Dose | Schedule | Route of Administration | No. of Animals | Dosing solution |
|---|---|---|---|---|---|---|
| 1 | Vehicle only | — | BID | PO | 10 | — |
| 2 | Cyclophosphamide | 150 mg/kg | Q5D | IP | 10 | 15 mg/ml |
| 3 | Compound 29 | 25 mg/kg | BID | PO | 10 | 2.5 mg/ml |
| 4 | Compound 29 | 50 mg/kg | BID | PO | 10 | 5 mg/ml |

Dosing solutions were prepared on the day of study. Formulation was 0.5% methylcellulose/0.025% Tween-20 at dosing volume of 10 ml/kg based on animal weight on day of dosing. Animals were dosed orally twice daily (12 hours apart) for 18 consecutive days.

Results

While animals treated with the positive control compound, cyclophosphamide, lost weight this was not significant. None of the compounds tested at either dose had any effect on animal bodyweight.

Figure 8:
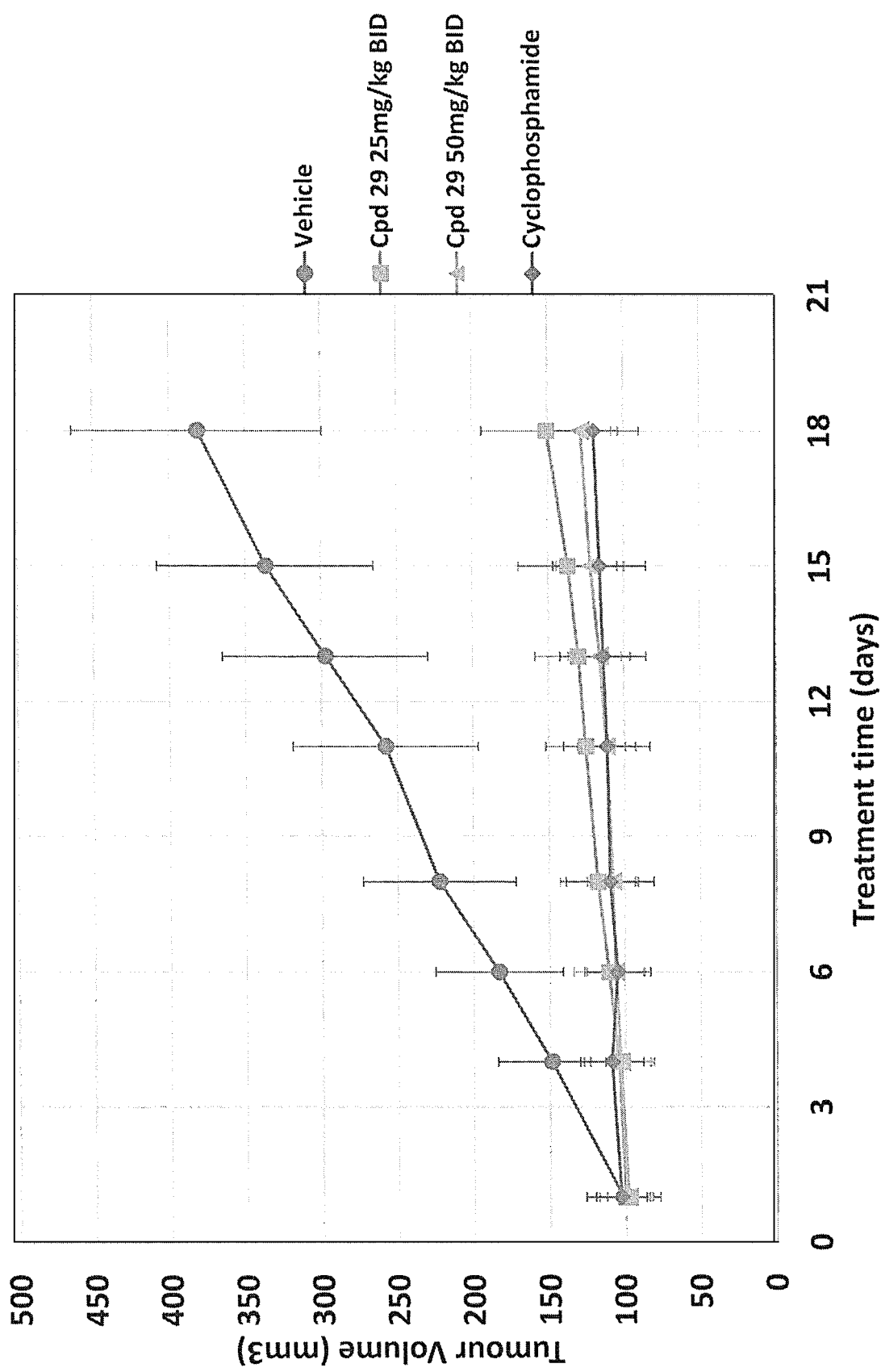
FIG. 8 is a plot of tumour volume against treatment time for male SCID mice bearing CCRF-HSB-2 tumours and treated with Compound 29 or cyclophosphamide.

Tumours in vehicle-treated animals grew steadily during the study (FIG. 8). Example 29 demonstrated good efficacy in controlling CCRF-HSB-2 tumour growth during the study, but both 25 and 50 mg/kg BID resulted in similar levels of tumour growth inhibition. At Day 18 mean tumour sizes in both treatment groups were not statistically different (p=0.6397, 2-way ANOVA with Tukey's post-hoc test).

At the end of the study period T/C (test versus control) values were 18.1% for Compound 29 at 25 mg/kg, 10.8% for Compound 29 at 50 mg/kg and 5.9% for cyclophosphamide.

Figure 9:
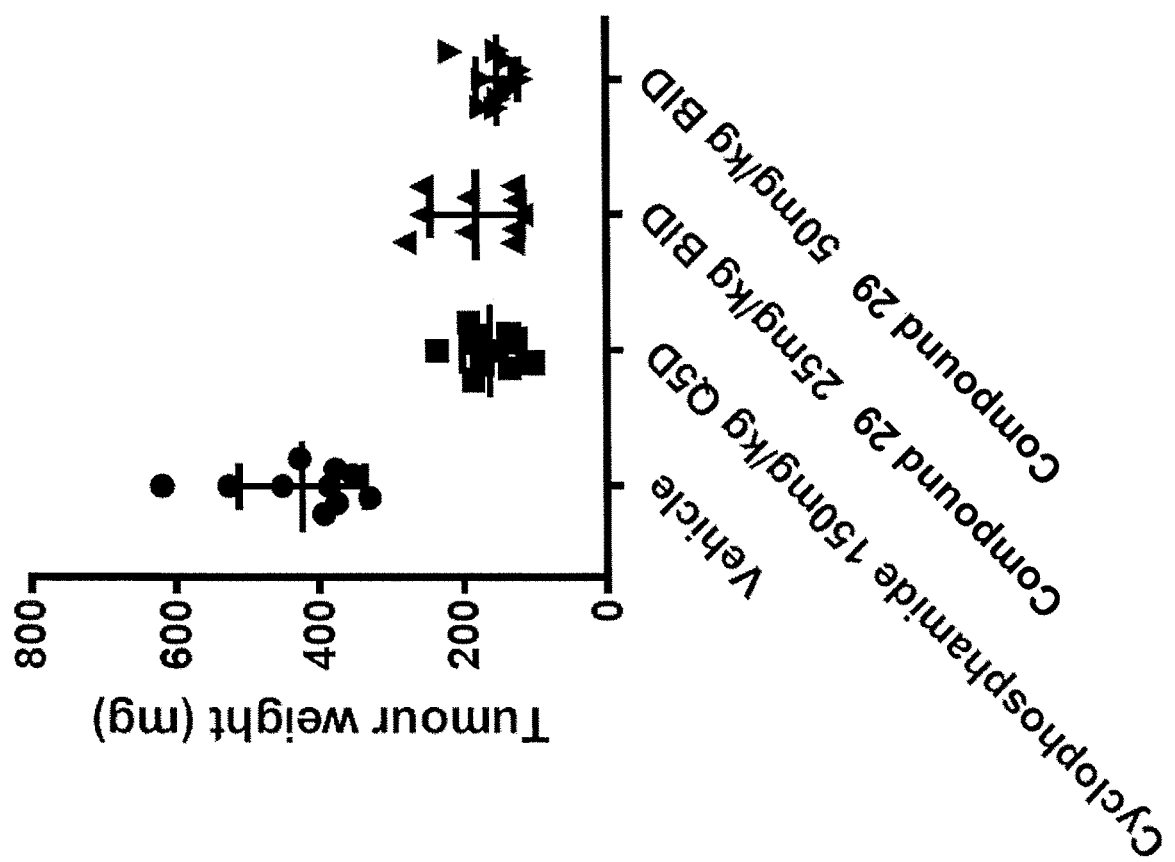
FIG. 9 is a plot of tumour weight for male SCID mice bearing CCRF-HSB-2 tumours treated with Compound 29 or cyclophosphamide.

At Day 18 tumour weight was significantly smaller in animals treated with Compound 29 at both 25 and 5 mg/kg BID than those observed in animals treated with vehicle only (p<0.0001, ANOVA with Tukey post-hoc test) (see FIG. 9).

Example 9

Tumour Growth Delay Study in Male SCID Mice Bearing MOLT-4 Xenografts

A total of 50 male SCID mice aged 5-7 weeks were used for the study. These were bred in-house at Axis Bioservices.

Animals were housed in IVC cages (up to 5 per cage) with individual mice identified by tail mark. All animals were allowed free access to a standard certified commercial diet and sanitised water during the study. The holding room was maintained under standard conditions: 20-24° C., 40-70% humidity and a 12 h light/dark cycle.

MOLT-4 cells ($1 \times 10^7$ in matrigel) were implanted onto the rear dorsum of male SCID mice using a 25-gauge needle. When tumours reached approximately 100-150 mm$^3$ the mice were randomly assigned to the following treatment groups.

| Group | Drug | Dose | Schedule | Route of Administration | No. of Animals |
|---|---|---|---|---|---|
| 1 | Vehicle only | — | BID | PO | 10 |
| 2 | Cyclophosphamide | 150 mg/kg | Q5D | IP | 10 |
| 3 | Compound 29 | 25 mg/kg | BID | PO | 10 |
| 4 | Compound 29 | 50 mg/kg | BID | PO | 10 |
| 5 | Compound 29 + Cyclophosphamide | 25 mg/kg + 150 mg/kg | BID + Q5D | PO | 10 |

Dosing solutions were prepared on the day of study. The formulation for Compound 29 was 0.5% methylcellulose/0.025% Tween-20 at a dosing volume of 10 ml/kg based on animal weight on day of dosing. The dosing matrix using this formulation was a milky suspension.

The formulation for cyclophosphamide was PBS at a dosing volume of 10 ml/kg based on animal weight on day of dosing. The dosing matrix using this formulation was a clear solution.

For combination dosing, both compounds were dosed at the same time.

Animals were dosed with Compound 29 orally twice daily (12 hours apart) for 21 consecutive days.

Results

Bodyweight in animals treated with Compound 29 at both 25 and 50 mg/kg was maintained at pre-treatment levels during the study. In animals receiving combination of Compound 29 at 25 mg/kg and cyclophosphamide, mean bodyweight decreased to a nadir of 91% pre-treatment levels before increasing slightly to 95% by the end of the study. One animal received a dosing holiday on Day 8. Although some bodyweight loss was observed, there were no adverse effects noted in terms of animal condition or behaviour during the study.

Figure 10:
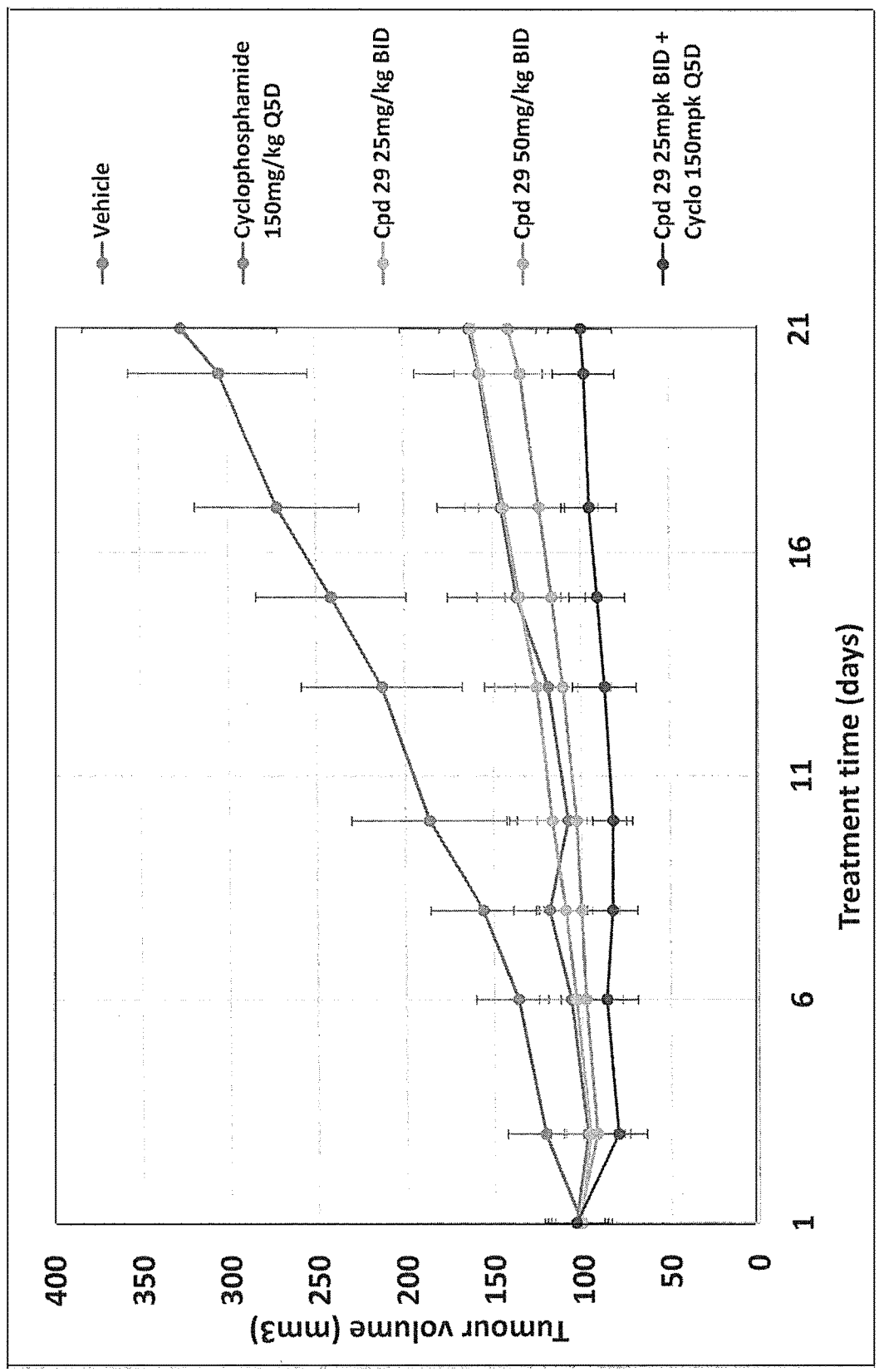
FIG. 10 is a plot of tumour volume against treatment time for male SCID mice bearing MOLT-4 tumours and treated with Compound 29, cyclophosphamide or a combination thereof.

Tumours in vehicle-treated animals grew steadily during the study (FIG. 10). At the end of the study, tumours from all treatment groups were significantly smaller than the vehicle control groups. ($p<0.0001$ for all groups; 2-way ANOVA with Tukey's post-hoc test). There was no significant difference between the monotherapy treatment groups at the end of study (2-way ANOVA with Tukey's post-hoc test). The tumours in the study using Compound 29 at 25 mg/kg BID in combination with cyclophosphamide 150 mg/kg Q5D group were significantly slower than the respective monotherapy groups ($p=0.0034$ compared to cyclophosphamide and 0.0043 compared to Compound 29 25 mg/kg QD by 2-way ANOVA with Tukey's post-hoc test).

At the end of the study period T/C (test versus control) values were 26.2% for cyclophosphamide, 16.6% for Compound 29 50 mg/kg BID, 26.8% for Compound 29 25 mg/kg BID and −2.1% for the combination group. All treatment groups show significant anti-cancer activity as defined by the NCI, which states that any compound which has a T/C value of less than or equal to 42% has demonstrated significant anti-cancer activity.

Figure 11:
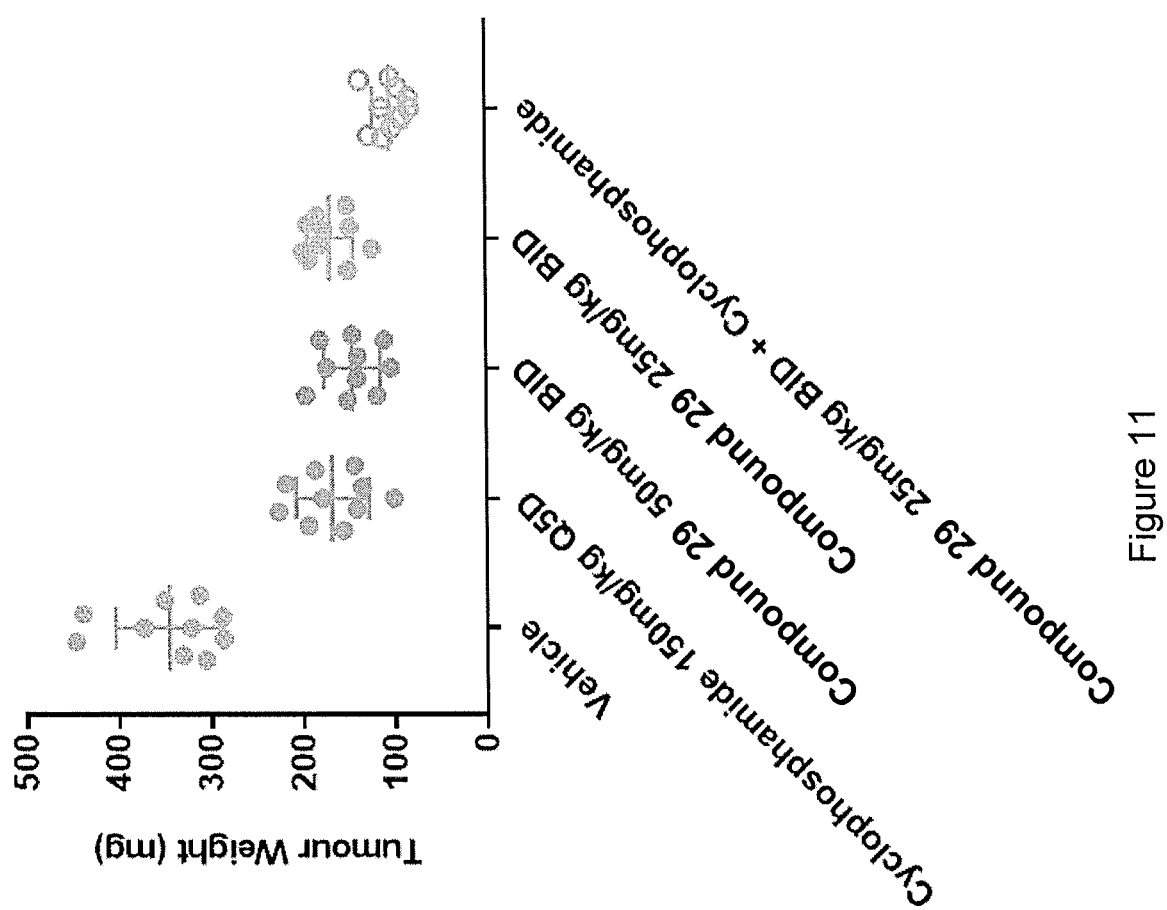
FIG. 11 is a plot of tumour weight for male SCID mice bearing MOLT-4 tumours treated with Compound 29, cyclophosphamide or a combination thereof.

Tumour tissue wet weight at the end of the study followed a similar pattern to measured tumour volume. Tumour weight in all treated groups was significantly lower than in vehicle controls ($p<0.0001$ in all cases, ANOVA with Tukey post-hoc test) (see FIG. 11).

Example 10

Pharmaceutical Formulations (i) Tablet Formulation

A tablet composition containing a compound of the formula (1) or formula (2) or a pharmaceutically acceptable salt thereof is prepared by mixing 50 mg of the compound with 197 mg of lactose (BP) as diluent, and 3 mg magnesium stearate as a lubricant and compressing to form a tablet in a known manner.

(ii) Capsule Formulation

A capsule formulation is prepared by mixing 100 mg of a compound of the formula (1) or formula (2) or a pharmaceutically acceptable salt thereof with 100 mg lactose and filling the resulting mixture into standard opaque hard gelatin capsules.

(iii) Injectable Formulation I

A parenteral composition for administration by injection can be prepared by dissolving a compound of the formula (1) or formula (2) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) or formula (2) (e.g. in salt form) (2 mg/mL) and mannitol (50 mg/mL), sterile filtering the solution and filling into sealable 1 mL vials or ampoules.

(iv) Sub-Cutaneous Injection Formulation

A composition for sub-cutaneous administration is prepared by mixing a compound of the formula (1) or formula (2) with pharmaceutical grade corn oil to give a concentration of 5 mg/mL. The composition is sterilised and filled into a suitable container.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of treating a cancer in a subject in need thereof by inhibiting TYK2 kinase in the subject, which method comprises administering to the subject a therapeutically effective amount of 2-(2,6-dichloro-phenyl)-5-[4-(morpholine-4-carbonyl)-phenylamino]-oxazole-4-carboxylic acid amide having the formula:

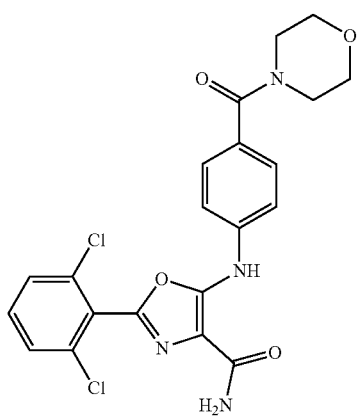 [SMILES: NC(=O)c1nc(-c2c(Cl)cccc2Cl)oc1Nc1ccc(C(=O)N2CCOCC2)cc1]

wherein:
the subject is a patient who has been diagnosed with a cancer that is susceptible to treatment with a TYK2 inhibitor and the cancer is selected from pancreatic, colorectal and kidney cancers, melanoma and B-cell lymphoma.

2. A method according to claim 1 which comprises administering the 2-(2,6-dichloro-phenyl)-5-[4-(morpholine-4-carbonyl)-phenylamino]-oxazole-4-carboxylic acid amide to the subject in combination with one or more further chemotherapeutic agents.

3. A method according to claim 2 wherein the one or more further chemotherapeutic agent comprises an alkylating agent.

4. A method according to claim 3 wherein the alkylating agent is cyclophosphamide.

5. A method according to claim 1 wherein the cancer that is susceptible to treatment with a TYK2 inhibitor is a cancer which is characterised by abnormally elevated levels of any one or more of phosphorylated STAT1, phosphorylated STAT3 and phosphorylated STAT5.

6. A method according to claim 1 wherein the cancer that is susceptible to treatment with a TYK2 inhibitor is a cancer which is characterised by abnormally elevated levels of BCL2.

7. A method according to claim 1 wherein the cancer that is susceptible to treatment with a TYK2 inhibitor is a cancer which is characterised by aberrant TYK2 kinase activation.

8. A method according to claim 1 wherein the cancer that is susceptible to treatment with a TYK2 inhibitor is a cancer which is characterised by aberrant TYK2 kinase activation associated with a TYK2 genomic rearrangement.

* * * * *